(12) United States Patent
Gründemann et al.

(10) Patent No.: US 8,492,106 B2
(45) Date of Patent: Jul. 23, 2013

(54) IDENTIFICATION METHODS FOR ERGOTHIONEINE TRANSPORTER MODULATORS AND THERAPEUTIC USES THEREOF

(75) Inventors: Dirk Gründemann, Brühl (DE); Edgar Schömig, Hürth (DE)

(73) Assignee: Universitat Zu Koln, Cologne (DE)

( * ) Notice: Subject to any disclaimer, the term of this patent is extended or adjusted under 35 U.S.C. 154(b) by 989 days.

(21) Appl. No.: 11/569,451

(22) PCT Filed: May 24, 2005

(86) PCT No.: PCT/EP2005/005613
§ 371 (c)(1),
(2), (4) Date: Jun. 25, 2007

(87) PCT Pub. No.: WO2005/116657
PCT Pub. Date: Dec. 8, 2005

(65) Prior Publication Data
US 2009/0214431 A1    Aug. 27, 2009

(30) Foreign Application Priority Data
May 24, 2004    (EP) .................................... 04012250

(51) Int. Cl.
*A61K 38/00*    (2006.01)
(52) U.S. Cl.
USPC ......................................................... 435/7.2
(58) Field of Classification Search
None
See application file for complete search history.

(56) References Cited

U.S. PATENT DOCUMENTS
2004/0197777 A1 * 10/2004 Peltekova et al. ................. 435/6

FOREIGN PATENT DOCUMENTS
| WO | 9836748 | 8/1998 |
| WO | WO 02/099053 A2 | 12/2002 |
| WO | WO 03/054011 A3 | 7/2003 |
| WO | 03082216 A2 | 9/2003 |
| WO | WO 2005/026737 A2 | 3/2005 |

OTHER PUBLICATIONS

Grundemann, D., et al., "Discovery of the ergothioneine transporter", PNAS, 102(14):5256-5261 (2005).
Search Report for co-pending PCT/EP2005/005613 listing relevant art cited by the International Searching Authority.

* cited by examiner

*Primary Examiner* — Robert Landsman
*Assistant Examiner* — Ian Dang
(74) *Attorney, Agent, or Firm* — McKee, Voorhees & Sease, P.L.C.

(57) ABSTRACT

The transporter that translocates ergothioneine has been identified. Described are methods for identifying and obtaining compounds capable of modulating ergothioneine transport as well as the use of such compounds for the treatment of diseases ergothioneine may be involved in such as autoimmune diseases, in particular rheumatoid arthritis, as well as other diseases arising from cell damage caused by radiation, radicals and relative oxidant species. Furthermore, diagnostic means and methods for determining the presence or susceptibility to such a disease are provided.

3 Claims, 4 Drawing Sheets proline betaine (stachydrine)

Ergothioneine carnitine glycine betaine

IDENTIFICATION METHODS FOR ERGOTHIONEINE TRANSPORTER MODULATORS AND THERAPEUTIC USES THEREOF

FIELD OF THE INVENTION

The present invention relates to transporter proteins involved in transport of substances from the outside to the inside of cells or vice versa. In particular, the present invention relates to the identification of the ergothioneine transporter and therapeutic uses thereof. Thus, the present invention concerns methods for identifying and obtaining compounds capable of modulating ergothioneine transport as well as the use of such compounds for the treatment of diseases ergothioneine may be involved in such as autoimmune diseases, in particular rheumatoid arthritis, as well as diseases arising from cell damage caused by radiation, radicals and reactive oxygen species.

BACKGROUND OF THE INVENTION

Organic cation compounds are moved across renal tubular epithelial cell membranes by multiple specific transporters, including a membrane potential-dependent transporter at the basolateral membrane and a proton/organic cation antiporter at the brush border membrane. Recently, the involvement of various transporters localized on the plasma membrane in the uptake system for nutrients and endogenous substances into cells and their transport mechanisms have been clarified (Tsuji and Tamai, Pharm. Res. 13 (1996), 963-977). These transporters recognize the structures of substances to be transported to selectively transport specific substances. Transporters that recognize the relatively wide range of structures may possibly recognize foreign substances such as drugs by mistake, and actively take in them into cells. It is believed that drugs permeate through the plasma membrane fundamentally by simple diffusion depending on their physicochemical properties such as molecular size, hydrophobicity, and hydrogen-binding capacity. Particularly, in the case of ionic drugs, only molecules in the non-dissociated form can permeate through the plasma membrane according to the pH partition hypothesis. However, it has become evident that a number of drugs penetrate through the cell membrane by a specific mechanism other than simple diffusion, that is, an active transport mediated by transporters, in organs that require efficient exchange of intracellular and extracellular substances, including, small intestine, uriniferous tubule, placenta, epithelial cells of choroid plexus, hepatocytes, and blood-brain barrier. Recently, cDNAs of several transporters have been cloned by the expression cloning method using *Xenopus* oocytes, a foreign gene expression system, and structural homology among them has been revealed (Fei et al., Nature 368 (1994), 563-566). For example, Gründemann et al. cloned an organic cation transporter, OCT1, which is assumed to be localized on a basement membrane, using the expression cloning method in 1994 (Gründemann et al., Nature 372 (1994), 549-552). Subsequently, OCT2 was identified by homology cloning based on the sequence of OCT1 (Okuda et al., Biochem. Biophys. Res. Commun. 224 (1996), 500-507). OCT1 and OCT2 show homology as high as 67% to each other (Gründemann et al., J. Biol. Chem. 272 (1997), 10408-10413). Both of them are intensely expressed in the kidney, but differ in the organ distribution; OCT1 is also expressed in the liver, colon, and small intestine, while OCT2 expression is specific to the kidney.

In 1996 Schömig and colleagues cloned a cDNA from cell line CAKI-1, a human kidney carcinoma cell line (DSMZ No. ACC 142) encoding a human putative integral membrane transport protein designated UT2h showing sequence similarity to organic cation transporter genes; see GenBank accession number Y09881.1 [GI:12053560]. More recently, Tamai et al., FEBS Lett. (1997), 107-111, reported on the cloning of a substantially identical cDNA encoding SLC22A4, which they named OCTN1. The deduced 551-amino acid protein contains 11 predicted transmembrane domains, a nucleotide-binding site motif, a motif conserved in sugar transporters, 4 potential N-glycosylation sites, and 5 potential protein kinase C phosphorylation sites. OCTN1 is 33% identical to OCT2 (SLC22A2) and 31% identical to OCT1 (SLC22A1). Recombinant OCTN1 expressed in mammalian cells has been reported to exhibit saturable uptake of the organic cation model substrate tetraethyl ammonium (TEA). TEA uptake was pH sensitive, with higher activity occurring at neutral and alkaline pH than at acidic pH. Depletion of cellular ATP decreased TEA uptake, indicating that OCTN1 transport occurs at least partially through an active process; the ATP dependence was greatest at acidic pH. Northern blot analysis detected a less than 2.5-kb OCTN1 transcript in several human fetal and adult tissues, with the highest expression levels found in fetal liver and adult kidney, trachea, and bone marrow. OCTN1 was also strongly expressed in several human cancer cell lines. Tamai et al. (1997) suggested that OCTN1 is a renal proton/organic cation antiporter functioning at the epithelial apical membrane. Similarly, international application WO99/13072 inter alia describes a human and a mouse gene, respectively, significantly homologous to organic cation transporter OCT1, encoding a transporter protein having organic cation transport activity for tetraethylammonium (TEA) and carnitine.

However, the biological implications of this organic cation transporter has not yet been elucidated.

International application WO03/054011 inter alia describes that genetic markers based on coding sequence mutations in the OCTN1 gene that significantly reduces its ability to transport the organic cation carnitine are associated with inflammatory bowel diseases such as severe, early-onset Crohn's Disease (CD). Recently, Tokuhiro et al., Nature Genetics 35 (2003), 341-348, reported on a significant association between SLC22A4 and rheumatoid arthritis, a common inflammatory disease with complex genetic components, in the Japanese population. They showed that expression of SLC22A4 is specific to hematologic and immunologic tissues and that SLC22A4 is also highly expressed in the inflammatory joints of mice with collagen-induced arthritis. A SNP affects the transcriptional efficiency of SLC22A4 in vitro, owing to an allelic difference in affinity to Runt-related transcription factor-1 (RUNX1), a transcriptional regulator in the hematopoietic system. A SNP in RUNX1 was also strongly associated with rheumatoid arthritis. However, the biological role of the SLC22A4 or OCTN1, in particular in view of its seemingly non-specificity for organic compounds remained unclear. Furthermore, the nature of the putative natural substrate molecules, if any, as well as the question whether generally an increase or decrease of transporter activity or selectively for only one such substrate molecule may be involved in disease processes remained still unknown. In addition, others published that the substrate specificity of OCTN1 was completely unresolved until now; see, e.g., di San Filippo et al., J. Biol. Chem. 278 (2003), 47776-47784. In fact, the OCTN1 remained the only organic cation transporter for which no endogenous compound has been found so far; see also review by Koepsell et al., Rev. Physiol. Biochem. Pharmacol. 150 (2003), 36-90, in particular table 3.

In view of the above, the technical problem underlying the present invention is to elucidate the substrate specificity of organic cation transporter OCTN1 (SLC22A4), which allows therapeutic intervention for disorders that are related to the malfunction or the lack of this transporter.

The solution to said technical problem is achieved by providing the embodiments characterized in the claims, and described further below.

SUMMARY OF THE INVENTION

The present invention is directed to the identification of the ergothioneine transporter (ETT) and therapeutic uses thereof. Hence, in one embodiment the present invention relates to a method for identifying and/or obtaining a compound capable of modulating ergothioneine transport, comprising contacting a test compound with a system for measuring ergothioneine transport activity, which system comprises an ergothioneine transporter (ETT) polypeptide or a functional fragment thereof, and a substrate for measuring ergothioneine transport by the system; and detecting an altered level of the ergothioneine transport activity of the ETT polypeptide or functional fragment in the presence of the test compound compared to the ergothioneine transport activity in the absence of the test compound and/or presence of a control. This method is useful to identify and obtain drugs for the treatment of disorders related to ETT transporter function or the lack of it as well as for determining the toxicity of a given compound, for example whether it blocks the ETT transporter activity. The impact of drug transporter studies on drug discovery and development is reviewed in Mizuno et al., Pharmacol. Rev. 55 (2003), 425-461.

Furthermore, the present invention relates to the use of a compound capable of modulating ergothioneine transport activity of the ETT for the manufacture of a medicament for the treatment and/or prophylaxis of a disease selected from the group consisting of diseases arising from cell damage due to radiation, radicals and reactive oxygen species. In particular, therapeutic intervention through ETT is envisaged for the treatment of autoimmune diseases, especially rheumatoid arthritis.

In a further aspect, the present invention relates to the use of a compound capable of modulating ergothioneine transport activity or expression of the ETT so as to reduce the intracellular level of ergothioneine in a target cell for the manufacture of a medicament for inducing cell death in a target cell, This embodiment is particularly suited for the treatment of malignant diseases, in particular cancer.

In addition, the finding of the ETT enables diagnostic methods for determining the presence of or a susceptibility to a disease or a disorder the ETT is involved in, which therefore is also subject of the present invention.

The present invention also concerns a nucleic acid molecule encoding an ergothioneine transporter (ETT) or a functional fragment thereof except for nucleic acid molecules consisting of a nucleotide sequence selected from SEQ ID NO: 1, a nucleotide sequence encoding the amino acid sequence of SEQ ID NO: 2 or a nucleotide sequence disclosed in Tokuhiro et al., Nat. Genet. 35 (2003), 341-348; European patent application EP-A-1020518 (international application WO99/13072) and international application WO03/054011, or a nucleotide sequence encoding an amino acid sequence disclosed in any one of those documents.

The identification of the substrate specificity of ETT now also enables the person skilled in the art to prepare functional derivatives of the originally described organic cation transporter polypeptides. Therefore, in a still further aspect the present invention relates to nucleic acid molecules encoding an ergothioneine transporter (ETT) and functional fragments thereof insofar said nucleic acid molecules do not consist of a nucleotide sequence that has been described prior to the present invention. In this context, the present invention also relates to vectors comprising such nucleic acid molecules as well as to host cells harbouring a corresponding vector. Furthermore, the provision of recombinant ETT polypeptides is envisaged as well as of antibodies specifically recognizing the ETT of the present invention.

DETAILED DESCRIPTION OF THE INVENTION

Figure 1:
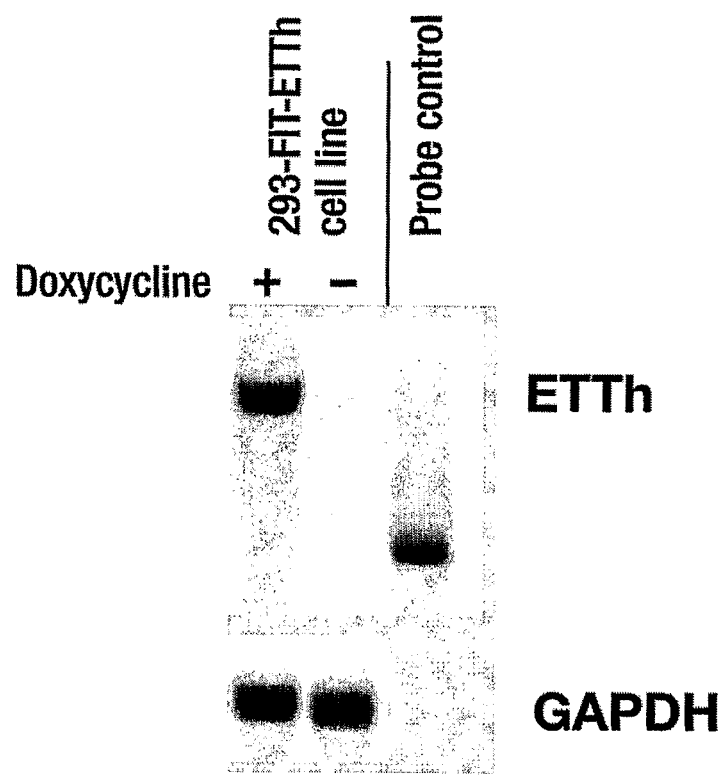
FIG. 1: Northern blot analysis of poly(A)$^+$ RNA (2 µg per lane) isolated from cell line 293-FIT-ETTh grown in the presence or absence of 1 µg/ml doxycycline for 48 h. The blot was probed first with a $^{35}$S-labeled single-stranded antisense ETTh DNA fragment, and second with an antisense $^{35}$S-labeled GAPDH fragment to control RNA loading of lanes. Quantification with a Fuji BAS radioluminography device revealed an intensity ratio basal/induced of ETTh mRNA of 0.9%.

The present invention generally relates to the ergothioneine transporter (ETT) and to various uses thereof, for example in therapeutic and diagnostic applications as well as research tool.

The present invention is based on the observation that the substrate of the organic cation transporter, previously known as OCTN1 (SLC22A4), contrary to what was reported in the prior art is ergothioneine (2-mercaptohistidine trimethylbetaine), a sulfur-containing amino acid which is radioprotective, antimutagenic, and scavenges singlet oxygen, hypochlorous acid (HOCl), hydroxyl radicals, and peroxyl radicals. Thus, the present invention for the first time identified a transporter capable of transporting ergothioneine into a cell, i.e. the ergothioneine transporter (ETT).

Without intending to be bound by theory it is believed that many, if not all health benefits and disease preventions currently employing ergothioneine for example in the form of a dietary supplement are a amenable to the treatment through the ergothioneine transporter disclosed in accordance with the present invention. Accordingly, any disease or condition which hitherto is treated with ergothioneine or envisaged for such treatment is also a disease or condition to be treated in accordance with the present invention through the ergothioneine transporter, for example using a drug that is capable of enhancing the ergothioneine transport activity, i.e. uptake of ergothioneine by the cell. Of course, also joint applications of ergothioneine and compounds which enhance ETT activity are envisaged herein. Diseases and conditions in relation to ergothioneine are described in the prior art; see WO98/36748 for the protection of mitochondria; WO03/082216 for protecting a mammalian central nervous system cell from damage and for the treatment and amelioration of neurodegenerative diseases; WO03/099277 for reducing incidence of diabetic embryopathy; as well as others; see also for example the compound monograph for L-ergothioneine by Oxis International, Inc.

L-ergothioneine (2-mercaptohistidine trimethylbetaine) ("ergothioneine") (FIG. 4) is a sulfur-containing amino acid formed via hercynine from histidine, methionine and cysteine in microorganisms. L-ergothioneine is not biosynthesized in animals, and thus is obtained only from dietary sources. Blood concentrations of ergothioneine in almost every species investigated are in near millimolar range (Table 1). The L-ergothioneine concentration in man is estimated to be in the range 46 µM to 183 µM.

TABLE 1

Blood concentration of ergothioneine in various animals.

| Species | Ergothioneine concentration (mg/100 ml blood) |
|---|---|
| Man | 1-4 |
| Rat | 1-6 |
| Rabbit | 1-10 |
| Guinea Pig | 1-4 |
| Cat | 0.5-2 |
| Dog | 3-6 |
| Ox | 0.5-2 |
| Pig | 3-27 |
| Sheep | 2-6 |
| Fowl | 2-10 |

Ergothioneine, i.e. 1-(+)- or L-ergothioneine is radioprotective, antimutagenic, and scavenges singlet oxygen, hypochlorous acid (HOCl), hydroxyl radicals, and peroxyl radicals (Hartman, Meth. Enzymol. 259 (1990), 310-318; Akanmu et al. Arch. Biochem. Biophys. 288 (1991), 10-16). Ergothioneine inhibits peroxynitrite dependent nitration of the amino acid tyrosine and DNA, and confers cellular homeostasis in neuronal cells challenged with the mixture of N-acetyl cysteine/hydrogen peroxide (Aruoma et al., Food Chem. Toxicol. 37 (1999), 1043-1053). Ergothioneine also inhibits the formation of xanthine and hypoxanthine, which may have many implications for inflammatory conditions such as gout, a condition characterized by overproduction of uric acid (the oxidation product of xanthine) (Aruoma et al., Food Chem. Toxicol. 37 (1999), 1043-1053).

Figure 4:
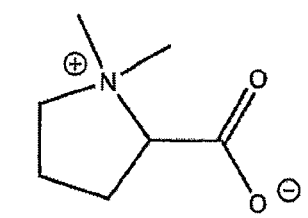
FIG. 4: Substrate structures.
Figure 4:
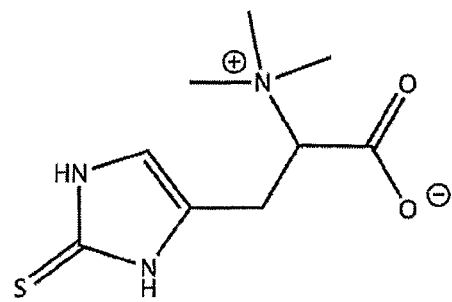
Figure 4:
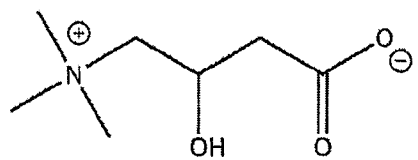
Figure 4:
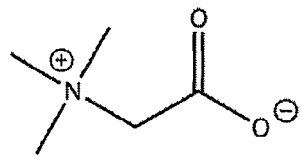

"Analog" and/or "derivative" of ergothioneine as used herein, refer to a synthetic organic compound, a nucleotide, or a peptide that possesses similar or identical activity or function(s) as the compound (ergothioneine) having the desired activity and therapeutic effect of the present invention and being transported by the ETT to a substantially similar extent as ergothioneine, but need not necessarily possess a structure that is similar or identical to that of ergothioneine; see also FIG. 4.

As used herein, the term "ergothioneine transporter" or "ETT" refers to an integral membrane transport protein first identified by the present inventors and called UT2h, the corresponding cDNA sequence of which has been deposited in the public EMBL/GenBank data base (accession number Y09881 [gi:12053560]); see also SEQ ID NO: 1. In 1997, Tamai et al., FEBS Lett. 419 (1997), suggested the designation OCTN1 ("novel organic cation transporter"), which hitherto has been commonly used; see also background section, supra. The closest relative of OCTN1 (gene symbol SLC22A4, which refers to Solute Carrier Family 22 Member 4-Transporter) is the carnitine carrier UST2/OCTN2 (gene symbol SLC22A5); see Schömig et al., FEBS Lett. 425 (1998), 79-86 and Tamai et al., J. Biol. Chem. 273 (1998), 20378-20382. Sequence alignment of OCTN1 and OCTN2 reveals a basic similarity, but also shows clear differences which are each conserved among human and rat. OCTN1 was also cloned from rat and mouse (Tamai et al. 1997, 2000; Wu et al., Biochim. Biophys. Acta 1466 (2000), 315-327; Yabuuchi et al., J. Pharmacol. Exp. Ther. 289 (1999), 768-773). The mouse gene corresponding to the human ETT is also described in international application WO99/13072; see the nucleotide sequence of the isolated cDNA as shown in SEQ ID NO: 23 (designated as "mouse OCTN1").

FIG. 1 of international application WO99/13072 represents hydrophobicity plots of human OCTN1 and human OCTN2 according to Kyte & Doolittle's calculating formula with a window of nine amino acid residues (Kyte and Doolittle, J. Mol. Biol. 157 (1982), 105-132), which very closely resembled those of OCT1 (Gründemann et al., Nature 372 (1994, 549-552) and OCT2, indicating that the sequence has eleven to twelve putative transmembrane hydrophobic regions numerals on the plots indicate putative transmembrane regions. This sequence contained one consensus sequence of sugar transporter, which is present in the glucose transporters GLUT1 to GLUT7 in mammalian cells, and also present in various types of transporters other than glucose transporters (Maiden et al., Nature 325 (1987), 641-643). Furthermore, putative N-linked glycosylation sequences (N-X-[ST]) were found in the amino acid sequence of human OCTN1 at four sites (57 to 59, 64 to 66, 91 to 93, and 304 to 306), and also five putative protein kinase C phosphorylation sites ([ST]-X-[RK]) (164 to 166, 225 to 227, 280 to 282, 286 to 288, and 530 to 532). In addition, the consensus sequence ([Ala, Gly]-Xaa(4)-Gly-Lys-[Ser, Thr]) of the ATP/GTP binding site is also found. This consensus sequence of the ATP/GTP binding site is also present in the ATP binding protein or GTP binding protein, such as kinases and ras family proteins, and that ATP or GTP binds to this site (Walker et al., EMBO J. 1 (1982, 945-951). This sequence is present in the so-called ATP Binding Cassette (ABC) type transporter, and involved in the substance transport using the energy generated by hydrolysis of ATP (Higgins et al., J. Bioenerg. Biomembr. 22 (1990), 571-592; Urbatsch et al., J. Biol. Chem. 270 (1995), 26956-26961). The presence of this consensus sequence indicates that OCTN1 protein may be an ATP or GTP-dependent transporter.

In the remainder of the description the previously designated OCTN1 transport protein (gene symbol SLC22A4) is referred to solely as ergothioneine transporter or ETT (ergothioneine transporter); the human orthologue may be specifically designated ETTh.

In one aspect, the present invention relates to a method for identifying and/or obtaining a compound capable of modulating ergothioneine transport comprising contacting a test compound with a system for measuring ergothioneine transport activity, which system comprises an ergothioneine transporter (ETT) polypeptide or a functional fragment thereof, and a substrate for measuring ergothioneine transport by the system; and detecting an altered level of the ergothioneine transport activity of the ETT polypeptide or functional fragment in the presence of the test compound compared to the ergothioneine transport activity in the absence of the test compound and/or presence of a control.

The nucleotide and amino acid sequences of ETT are described in the prior art and are exemplified in SEQ ID NO: 1 and 2, respectively; see also supra. Naturally, the system employed in the method of the present invention is a cell-based system. Accordingly, a promoter and/or enhancer is usually employed that effectively directs the expression of the polynucleotide encoding ETT in the test cell; see also Example 1. Those skilled in the art of molecular biology generally know how to use promoters, enhancers and cell-type combinations for protein expression, for example, see Sambrook et al. (1989) and Ausubel et al. (1994), infra. The promoters employed are preferably inducible and useful under appropriate conditions to direct high-level expression of the ETT polynucleotide. Inducible promoters are particularly preferred since the experiments performed in accordance with the present invention showed that there might be a negative selection against a constitutive high-level expression of ETT; see Example 1. The use of an inducible promoter in the present invention provides a molecular switch capable of turning on expression of the polynucleotide sequence which is operatively linked when such expression is desired, or turning off the expression when expression is not desired. Examples of inducible promoters include, but are not limited to a metallothioneine promoter, a glucocorticoid promoter, a progesterone promoter and a tetracycline promoter. Numerous expression vector systems exist that can be employed for use with the present invention. For example, Stratagene's Complete Control™ relates to an inducible mammalian expression system, which involves a synthetic ecdyson-inducible promoter. Another example of an inducible expression system is available from Invitrogen, which carries the T-REX™ (tetracycline-regulated expression) system, an inducible mammalian expression system that uses the full-length CMV promoter.

For determining whether or not a given compound is capable of modulating the ETT in accordance with the present invention, the ergothioneine transport activity, i.e. level of substrate such as ergothioneine in the test cell and/or medium may be compared with standard values obtained for example with a corresponding assay performed in the absence of the test compound. Detection of the level of the ergothioneine transport activity of the ETT can be performed according to methods well-known in the art; see also Examples 3 and 4. An assay for uptake and antioxidant effects of ergothioneine in human erythrocytes is described Mitsuyama and May in Clinical Science 97 (1999), 407-411.

The terms "compound" and "agent" are used interchangeably herein and refer to all materials that may be used to prepare pharmaceutical compositions and/or that may be synthetic organic compounds, nucleic acids, polypeptides, fragments, isoforms, variants, or other materials that may be used independently for such purposes, all in accordance with the present invention. In particular, the term "compound" is taken to include both organic compounds such as peptides, as well as inorganic compounds such as ion chelators. Antibodies, e.g., polyclonal or monoclonal antibodies directed against ETT protein, the Fab, Fab', F(ab') fragments of such antibodies, as well as single-chain anti-ETT antibodies can also be considered as compounds of the present methods.

The compound capable of modulating the ETT may either enhance the transporter function of ETT, i.e. it is an "agonist/activator", or it may reduce and block, respectively, the transporter function of ETT, i.e. it is an "antagonist/inhibitor".

The terms "antagonist/inhibitor" and "agonist/activator" in accordance with the present invention include chemical agents that modulate the action of ETT, either through altering its enzymatic or biological activity or through modulation of expression, e.g., by affecting transcription or translation. In some cases the antagonist/inhibitor or agonist/activator may also be a substrate or ligand binding molecule or a derivative thereof.

The term "activator", as used herein, includes both substances necessary for ETT to become active in the first place, and substances which merely accentuate its activity.

The term "inhibitor" includes both substances which reduce the activity of the ETT and these which nullify it altogether. When more than one possible activity is defined herein for ETT, the inhibitor or activator may modulate any or all of ETT activities.

An "antagonist" or "agonist" that modulates the activity of ETT and causes for example a response in a cell based assay refers to a compound that alters directly or indirectly the activity of ETT or the amount of active ETT. Typically, the effect of an antagonist is substantially the same as that of anti-ETT antibodies described. Antagonists include competitive as well as non-competitive antagonists. A competitive antagonist (or competitive blocker) interacts with or near the site specific for agonist binding. A non-competitive antagonist or blocker inactivates the function of the promoter by interacting with a site other than the agonist interaction site. Furthermore, the agonist and antagonist, respectively, may bind intracellular or extracellular to the ETT polypeptide. A sort of premodeling or preselection of compounds that may serve as putative agonists or antagonists can be made according to the known structure of ETT; see the discussion with respect to the previous designation of the ergothioneine transporter OCTN1 above. Thus, the glycosylation and phosphorylation sites as well as the intracellular and in particular extracellular domain of ETT, respectively, are promising targets, especially for small molecules. Furthermore, FIG. 1 in Koepsell et al., Rev. Physiol. Biochem. Pharmacol. 150 (2003), 36-90, provides the amino acid sequence and current model of membrane topology for human electrogenic organic cation transporter hOCT1, indicating inter alia amino acids (a.a.) that are conserved in particular subfamilies of the SLC22 transporter family and consensus sequences for N-glycosylation or phosphorylation that are conserved in all functional members of the SLC22 family. This model may also serve for the design or pre-selection of putative agonists and antagonists in accordance with the present invention. Preferably, the antagonist/inhibitor and agonist/activator of ETT are small chemical agents which directly interact with ETT. Therefore, there will preferably be a direct relationship between the molar amount of compound required to inhibit or stimulate ETT activity and the molar amount of ETT present or lacking in the cell. ETT antagonists may be peptides, proteins, nucleic acids, antibodies, small organic compounds, peptide mimics, aptamers or PNAs (Milner, Nature Medicine 1 (1995), 879-880; Hupp, Cell 83 (1995), 237-245; Gibbs, Cell 79 (1994), 193-198; Gold, Ann. Rev. Biochem. 64 (1995), 736-797). For the preparation and application of such compounds, the person skilled in the art can use the methods known in the art, for example those referred to herein.

In one particular aspect, the present invention relates to a method for identifying and/or obtaining a compound for the treatment and/or prophylaxis of a disease related to the immune system comprising (a) contacting a test compound with a system for measuring ergothioneine transport activity, which system comprises an ETT polypeptide or a functional fragment thereof, and a substrate for measuring ergothioneine transport by the system; and (b) detecting an altered level of the ergothioneine transport activity of the ETT polypeptide or functional fragment in the presence of the test compound compared to the ergothioneine transport activity in the absence of the test compound and/or presence of a control.

This embodiment as well as the use of compounds identified by the method of the present invention, which are capable of modulating the transport activity of ETT are based on immunohistochemical experiments performed in accordance with the present invention, which demonstrated that ETT is expressed in bone marrow and leukocytes. Further experiments revealed that ETT is highly expressed in monocytes and macrophages, the latter being of particular importance in the defense of infectious agents and in the removal of cell debris. Without intending to be bound by theory it is therefore believed that ergothioneine has a certain function in monocytes and macrophages, for example in antagonizing a respiratory burst, i.e. free radicals and other oxidants which are produced in macrophages upon stimulation. In accordance with the present invention it is believed that in these cells ergothioneine acts as a scavenger for oxidizing molecules, in particular for the product of myeloperoxidase, i.e. hypochlorous acid (HOCl). A deficiency in intracellular levels of ergothioneine would therefore result in a dysfunction of those cells. Accordingly, it is expected that with the help of the ergothioneine transporter identified in accordance with the present invention macrophage function can be therapeutically modulated in both ways, i.e. by stimulation as well as by inhibition. Such modulation is particularly suited for the treatment of diseases cells of the immune system are involved in, i.e. autoimmune diseases such as rheumatoid arthritis, Morbus Crohn as well as others; see also infra.

In view of the fact that therapy concepts for treatment of autoimmune diseases hitherto available are insufficient or have certain drawbacks since they are exclusively directed against the symptoms of the respective autoimmune disease and often also display severe undesired side effects, the provision of the ergothioneine system in accordance with the present invention contributes a novel target for the development and application of medical therapies for the treatment and prevention of autoimmune diseases as well as for the diagnosis of the same. Further embodiments which have been developed from the findings of the present invention are described further below.

In one embodiment, said compound is an anti-ETT antibody which may act as an agonist or antagonist, depending on the target epitope of ETT. Said antibody can be, for example, a monoclonal antibody, a polyclonal antibody, a single chain antibody, a fully human antibody, a humanized antibody, a xenogeneic antibody or fragment thereof that specifically binds said ETT peptide or polypeptide also including bispecific antibody, synthetic antibody, antibody fragment, such as Fab, Fv or scFv fragments etc., or a chemically modified derivative of any of these. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the ETT polypeptide (Schier, Human Antibodies Hybridomas 7 (1996), 97-105; Malmborg, J. Immunol. Methods 183 (1995), 7-13). The production of chimeric antibodies is described, for example, in WO89/09622. Methods for the production of humanized antibodies are described in, e.g., EP-A1 0 239 400 and WO90/07861. A further source of antibodies to be utilized in accordance with the present invention are so-called xenogenic antibodies. The general principle for the production of xenogenic antibodies such as human antibodies in mice is described in, e.g., WO91/10741, WO94/02602, WO96/34096 and WO96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. It is particularly preferred that the antibodies/antibody constructs are employed in intracellular settings. Such antibody constructs/antibodies are well known in the art and are, inter alia, described in Lener, Eur. J. Biochem. 267, (2000), 1196-1205, who described intracellular antibodies against p21 ras.

In another embodiment of the present invention said antagonist is based on nucleic acids, for example a ribozyme, aptamers, antisense or sense nucleic acid molecules to the ETT gene or dsRNA molecules which are capable of mediating RNA interference. Methods and computer programs for the preparation rational selection of for example antisense oligonucleotide sequences are described in the prior art; see for example Smith, Eur. J. Pharm. Sci. 11(2000), 191-198; Toschi, Methods 22 (2000), 261-269; Sohail, Adv. Drug Deliv. Rev. 44 (2000), 23-34; Moulton, J. Comput. Biol. 7 (2000), 277-292. These methods can include the more empirical testing of large numbers of mRNA complementary sequences to the more systematic techniques, i.e. RNase H mapping, use of combinatorial arrays and prediction of secondary structure of mRNA by computational methods. Structures that bind to structured RNA, i.e. aptastructures and tethered oligonucleotide probes, and foldback triplex-forming oligonucleotides can also be employed for the purpose of the present invention. Relating to selection of antisense sequences by aid of computational analysis, sources for valuable www addresses are given below.

As described in Example 3, it could be determined in accordance with the present invention that the substrates of ETT must contain a glycine betaine moiety. In particular, it could be shown that besides ergothioneine also proline betaine and hydroxyproline betaine as well as some other glycine betaine moiety-containing compounds are good substrates for the ETT. Thus, while ergothioneine is the preferred substrate for use in the methods of the present invention, generally the substrate for measuring ergothioneine transport is selected from the group consisting of ergothioneine, proline betaine, hydroxyproline betaine or a derivative or analog of any one thereof, wherein said derivative or analog comprises a glycine betaine moiety; see also FIG. 4.

While the reconstitution of membrane vesicles with functional ergothioneine transporter polypeptide for use in the methods of the present invention may be feasible, naturally cell-based assays are preferred. Thus, the screening methods of the present invention will usually employ cells, preferably eukaryotic cells and most preferably mammalian cells, which are genetically engineered to express the ETT polypeptide. In particular, an ETT polypeptide is usually employed which is encodable by a polynucleotide selected from the group consisting of:

(a) polynucleotides encoding at least the mature form of the polypeptide comprising the amino acid sequence depicted in SEQ ID NO: 2;
(b) polynucleotides comprising the coding sequence as depicted in SEQ ID NO: 1 encoding at least the mature form of the polypeptide;
(c) polynucleotides encoding a polypeptide derived from the polypeptide encoded by a polynucleotide of (a) or (b) by way of substitution, deletion and/or addition of one or several amino acids of the amino acid sequence encoded by the polynucleotide of (a) or (b);
(d) polynucleotides the complementary strand of which hybridizes with a polynucleotide of any one of (a) to (c);
(e) polynucleotides encoding a polypeptide the amino acid sequence of which has an identity of 60% or more to the amino acid sequence of the polypeptide encoded by a polynucleotide of any one of (a) to (d);
(f) polynucleotides encoding a polypeptide capable of ergothioneine transport comprising a fragment or an epitope-bearing portion of a polypeptide encoded by a polynucleotide of any one of (a) to (e);
(g) polynucleotides comprising at least 15 consecutive nucleotides of a polynucleotide of any one of (a) to (f);
(h) polynucleotides obtainable by screening an appropriate library under stringent conditions with a probe having at least 15 consecutive nucleotides of a polynucleotide of (a) or (b);
(i) polynucleotides comprising a nucleotide sequence which is degenerated as a result of the genetic code to a nucleotide sequence of a polynucleotide of any one of (a) to (h).

An ETT polypeptide capable of ergothioneine transport refers to polypeptides exhibiting activity similar, but not necessarily identical to, an activity of an ETT polypeptide as measured in a particular biological assay such as described in the appended examples, with or without dose dependency. In the case where dose dependency does exist, it need not be identical to that of the ETT polypeptide, but rather substantially similar to the dose-dependence in a given activity as compared to the ETT polypeptide (i.e., the candidate polypeptide will exhibit greater activity or not more than about 25-fold less and, preferably, not more than about ten-fold less activity, and most preferably, not more than about three-fold less activity relative to the ETT polypeptide).

In this context, the identification of the ergothioneine transporter for the first time enables the person skilled in the art to produce functional analogs and derivatives of said transporter. Therefore, the present invention for the first time provides polynucleotides as defined in (c) to (i), supra, which encode functional ETT polypeptides. Accordingly, the present invention also relates to such hitherto unknown polynucleotides as defined above encoding organic cation transporters specific for ergothioneine. Thus, the present invention relates to a nucleic acid molecule encoding an ergothioneine transporter (ETT) or a functional fragment thereof comprising a polynucleotide as defined above except for a polynucleotide consisting of a nucleotide sequence selected from SEQ ID NO: 1, nucleotide sequences encoding the amino acid sequence of SEQ ID NO: 2 and the nucleotide sequences disclosed in Tokuhiro et al., Nat. Genet. 35 (2003), 341-348; European patent application EP-A-1020518 and international application WO03/054011, and nucleotide sequences encoding an amino acid sequence disclosed in any one of those documents.

The ETT proteins of this invention also include those having the additional activity to transport substances other than organic cations as far as they retain the ergothioneine transport activity. Organic cations include, for example, carcinostatic agents such as actinomycin D, etoposide, vinblastine, daunomycin, etc. Transporter proteins of this invention include those having the activity to transport organic cations not only from the outside to the inside of cells but also from the inside to the outside of cells.

The terms "epitope-bearing", "immunologically active" or "immunological activity" refers to fragments, analogues and derivatives of the ETT polypeptide the essential characteristic immunological properties of which remain unaffected in kind, that is that the nucleic acid molecules of the invention include all nucleotide sequences encoding proteins or peptides which have at least a part of the primary and/or secondary structural conformation for one or more epitopes capable of reacting specifically with antibodies unique to ETT protein which is encodable by a nucleic acid molecule as set forth above. Preferably, the peptides and proteins encoded by the nucleic acid molecule are recognized by an antibody that specifically reacts with an epitope of the ETT polypeptide comprising the amino acid residues depicted in SEQ ID NO: 2. Preferably, the immunologically active ETT peptide fragments, analogues and derivatives of the ETT polypeptide of the invention are capable of eliciting an immune response in a mammal, preferably in mouse or rat.

By the provision of the nucleotide sequence of SEQ ID NO: 1 and the amino acid sequence of SEQ ID NO: 2, respectively, and the identification of the substrate specificity of the transporter protein, it is now possible to isolate identical or similar polynucleotides which encode proteins with the biological activity of ETT from other species or organisms. Said polynucleotide sequences may be employed in accordance with this invention in the pharmaceutical compositions, uses and/or methods described herein. Well-established approaches for the identification and isolation of such related sequences are, for example, the isolation from genomic DNA or cDNA libraries using the complete or part of the disclosed sequence as a probe or the amplification of corresponding polynucleotides by polymerase chain reaction using specific primers; see, e.g. Schuler, Genome Research 7 (1997), 541-550. Thus, the invention also relates to polynucleotides which hybridize to the above described polynucleotides and differ at one or more positions in comparison to these as long as they encode an ETT protein as defined above. Such molecules comprise those which are changed, for example, by deletion(s), insertion(s), alteration(s) or any other modification known in the art in comparison to the above described polynucleotides either alone or in combination. Methods for introducing such modifications in the polynucleotides of the invention are well-known to the person skilled in the art; see, e.g., Sambrook et al. (Molecular cloning; A Laboratory Manual, Second Edition, Cold Spring Harbor Laboratory Press, Cold Spring Harbor N.Y. (1989)). The invention also relates to polynucleotides the nucleotide sequence of which differs from the nucleotide sequence of any of the above described polynucleotides due to the degeneracy of the genetic code.

With respect to the polynucleotides characterized under (d) above, the term "hybridizing" in this context is understood as referring to conventional hybridization conditions, preferably such as hybridization in 50% formamide/6×SSC/0.1% SDS/

100 μg/ml ssDNA, in which temperatures for hybridization are above 37° C. and temperatures for washing in 0.1×SSC/ 0.1% SDS are above 55° C. Most preferably, the term "hybridizing" refers to stringent hybridization conditions, for example such as described in Sambrook, supra. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. "Stringent hybridization conditions" and "stringent wash conditions" in the context of nucleic acid hybridization experiments depend upon a number of different physical parameters. The most important parameters include temperature of hybridization, base composition of the nucleic acids, salt concentration and length of the nucleic acid. One having ordinary skill in the art knows how to vary these parameters to achieve a particular stringency of hybridization. In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe; see Sambrook et al., page 9.51, hereby incorporated by reference.

The Tm for a particular DNA-DNA hybrid can be estimated by the formula:

$$Tm=81.5° C.+16.6(\log 10[Na^+])+0.41(\text{fraction G+C})- 0.63(\% \text{ formamide})-(600/l)$$

where l is the length of the hybrid in base pairs.

The Tm for a particular RNA-RNA hybrid can be estimated by the formula:

$$Tm=79.8° C.+18.5(\log 10[Na^+])+0.58(\text{fraction G+C})+ 11.8(\text{fraction G+C})2-0.35(\% \text{ formamide})- (820/l).$$

The Tm for a particular RNA-DNA hybrid can be estimated by the formula:

$$Tm=79.8° C.+18.5(\log 10[Na^+])+0.58(\text{fraction G+C})+ 11.8(\text{fraction G+C})2-0.05(\% \text{ formamide})- (820/l).$$

In general, the Tm decreases by 1–1.5° C. for each 1% of mismatch between two nucleic acid sequences. Thus, one having ordinary skill in the art can alter hybridization and/or washing conditions to obtain sequences that have higher or lower degrees of sequence identity to the target nucleic acid. For instance, to obtain hybridizing nucleic acids that contain up to 10% mismatch from the target nucleic acid sequence, 10–15° C. would be subtracted from the calculated Tm of a perfectly matched hybrid, and then the hybridization and washing temperatures adjusted accordingly. Probe sequences may also hybridize specifically to duplex DNA under certain conditions to form triplex or other higher order DNA complexes. The preparation of such probes and suitable hybridization conditions are well known in the art.

An example of stringent hybridization conditions for hybridization of complementary nucleic acid sequences having more than 100 complementary residues on a filter in a Southern or Northern blot or for screening a library is 50% formamide/6×SSC at 42° C. for at least ten hours. Another example of stringent hybridization conditions is 6×SSC at 68° C. for at least ten hours. An example of low stringency hybridization conditions for hybridization of complementary nucleic acid sequences having more than 100 complementary residues on a filter in a Southern or northern blot or for screening a library is 6×SSC at 42° C. for at least ten hours. Hybridization conditions to identify nucleic acid sequences that are similar but not identical can be identified by experimentally changing the hybridization temperature from 68° C. to 42° C. while keeping the salt concentration constant (6×SSC), or keeping the hybridization temperature and salt concentration constant (e.g. 42° C. and 6×SSC) and varying the formamide concentration from 50% to 0%. Hybridization buffers may also include blocking agents to lower background. These agents are well-known in the art; see Sambrook et al., pages 8.46 and 9.46-9.58, herein incorporated by reference.

Wash conditions also can be altered to change stringency conditions. An example of stringent wash conditions is a 0.2×SSC wash at 65° C. for 15 minutes; see Sambrook et al., for SSC buffer. Often the high stringency wash is preceded by a low stringency wash to remove excess probe. An exemplary medium stringency wash for duplex DNA of more than 100 base pairs is 1×SSC at 45° C. for 15 minutes. An exemplary low stringency wash for such a duplex is 4×SSC at 40° C. for 15 minutes. In general, signal-to-noise ratio of 2× or higher than that observed for an unrelated probe in the particular hybridization assay indicates detection of a specific hybridization.

The term "percent sequence identity" or "identical" in the context of nucleic or amino acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using NCBI BLASTx and BLASTn software. Alternatively, Fasta, a program in GCG Version 6.1. Fasta provides alignments and percent sequence identity of the regions of the best overlap between the query and search sequences (Pearson, 1990, herein incorporated by reference). For instance, percent sequence identity between nucleic acid sequences can be determined using Fasta with its default parameters (a word size of 6 and the NOPAMfactor for the scoring matrix) as provided in GCG Version 6.1, herein incorporated by reference.

Particularly preferred are polynucleotides which share 60 or 70%, preferably at least 85%, more preferably 90-95%, and most preferably 96-99% sequence identity with one of the above mentioned polynucleotides and have the same biological activity. Such polynucleotides also comprise those which are altered, for example by nucleotide deletion(s), insertion(s), substitution(s), addition(s), and/or recombination(s) and/or any other modification(s) known in the art either alone or in combination in comparison to the above described polynucleotides. Methods for introducing such modifications in the nucleotide sequence of the polynucleotide of the invention are well known to the person skilled in the art. Thus, the present invention encompasses any polynucleotide that can be derived from the above described polynucleotides by way of genetic engineering and that encode upon expression an ETT protein or a biologically active and/ or immunological active fragment thereof.

The ETT polynucleotide can be composed of any polyribonucleotide or polydeoxyribonucleotide, which may be unmodified RNA or DNA or modified RNA or DNA. For example, ETT polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the ETT polynucleotides can be composed of triple-stranded regions comprising RNA or DNA or both RNA and DNA. ETT polynucleotides may also contain one or more modified bases or DNA or RNA backbones modified for stability or for other reasons. "Modified" bases include, for example, trity-lated bases and unusual bases such as inosine. A variety of modifications can be made to DNA and RNA; thus, "polynucleotide" embraces chemically, enzymatically, or metabolically modified forms.

As a practical matter, whether any particular polypeptide is at least 40%, 50%, 60%, 70%, 80%; 90%, 95%, 96%, 97%, 98% or 99% identical to, for instance, the amino acid sequences shown in SEQ ID NO: 2 can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6 (1990), 237-245). In a sequence alignment the query and subject sequences are either both nucleotide sequences or both amino acid sequences. The result of said global sequence alignment is in percent identity. Preferred parameters used in a FASTDB amino acid alignment are: Matrix=PAM0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

Naturally occurring ETT variants are also encompassed in the present invention and are called "allelic variants," and refer to one of several alternate forms of a gene occupying a given locus on a chromosome of an organism; see, e.g., Genes II, Lewin, B., ed., John Wiley & Sons, New York (1985) and updated versions. These allelic variants can vary at either the polynucleotide and/or polypeptide level. Alternatively, non-naturally occurring variants may be produced by mutagenesis techniques or by direct synthesis.

If in the course of search in the database homology is found for ETT nucleotide sequences to "Expressed Sequence Tags" (ESTs), i.e. (partial) cDNA clones comprising Open Reading Frames (ORFs) for (fragments of) proteins of unknown function and/or the nucleotide sequence of which has not sufficient coding capacity for a functional protein, these particular ESTs per se are specifically excluded. However, as far as derivatives and the use of such ESTs in embodiments is concerned, which have been first conceived in accordance with the present invention, they are covered by the present invention and encompassed by the appended claims. The same applies to nucleotide sequences that may be present within, for example, a section of a chromosome that has been described in context with an organism's genome sequencing project but hitherto have not been identified to constitute a gene with a biological function.

In another embodiment the present invention relates to nucleic acid molecules specifically hybridizing to one of the nucleic acid molecules described above, wherein the latter encodes a mutated version of the ETT protein which has lost or is substantially reduced in its capability of transporting ergothioneine.

The nucleic acid molecules described above can be contained in a vector and preferably be operatively linked to regulatory elements permitting expression in prokaryotic or eukaryotic host cells. Expression of said nucleic acid molecule comprises transcription into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally associated or heterologous promoter regions.

Possible regulatory elements permitting expression in prokaryotic host cells comprise, e.g., the $P_L$, lac, trp or tac promoter in *E. coli*, and examples for regulatory elements permitting expression in eukaryotic host cells are the AOX1 or GAL1 promoter in yeast or the CMV-, SV40-, RSV-promoter, CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the nucleic acid molecule. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogen), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the protein so produced.

Furthermore, the present invention relates to vectors, particularly plasmids, cosmids, viruses and bacteriophages used conventionally in genetic engineering that comprise a nucleic acid molecule encoding an ETT polypeptide, wherein preferably the nucleic acid molecule is operably linked to an inducible expression control sequence; see also supra and Example 1. The tetracycline-inducible system for regulation of gene expression in transgenic mice is described in Grill et al., Transgenic Res. 12 (2003), 33-43. Furthermore, tetracycline-regulated gene expression in replication-incompetent herpes simplex virus vectors is described by Schmeisser et al., Hum. Gene Ther. 13 (2002), 2113-2124. In addition, the rapid generation of a tetracycline-inducible BCR-ABL defective retrovirus using a single autoregulatory retroviral cassette is provided in Dugray et al., Leukemia 15 (2001), 1658-1662. The use of the tetracycline-controlled transcriptional silencer (tTS) to eliminate transgene leak in inducible overexpression transgenic mice is described in Zhu et al., J. Biol. Chem. 276 (2001), 25222-25229. The Tet-On system in transgenic mice for inhibition of the mouse pdx-1 gene activity by antisense RNA expression in pancreatic beta-cells is reported by Lottmann et al., J. Mol. Med. 79 (2001), 321-328. For doxycycline inducible gene expression see, e.g., Lindeberg et al., J. Neurosci. Res. 68 (2002), 248-253 and Kim et al., Am. J. Pathol. 162 (2003), 1693-1707. Furthermore, the use of doxycycline-controlled gene expression to reversibly alter milkprotein composition in transgenic mice is described in Soulier et al., Eur. J. Biochem. 260 (1999), 533-539. All the inducible expression system can be employed in accordance with the vectors and methods of the present invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or a vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells. The vectors containing the ETT nucleic acid molecules can be transferred into the host cell by well known methods, which vary depending on the type of cellular host. For example, calcium chloride transfection is commonly utilized for prokaryotic cells, whereas calcium phosphate treatment or electroporation may be used for other cellular hosts; see Sambrook, supra.

Vectors that can be used for therapeutic and/or diagnostic purposes in accordance with the teaching of the present invention are known to the person skilled in the art; see, e.g., heritable and inducible genetic interference by double-stranded RNA encoded by transgenes described in Tavernarakis et al., Nat. Genet. 24 (2000), 180-183. Further vectors and methods for gene transfer and generation of transgenic animals are described in the prior art; see, e.g., adeno-associated virus related vectors described in Qing et al., Virol. 77 (2003), 2741-2746, and human immunodeficiency virus type 2 (HIV-2) vector-mediated in vivo gene transfer into adult rabbit retina described in Cheng et al. Curr. Eye Res. 24 (2002), 196-201. CNS gene transfer has also been described in Leone et al., Curr. Opin. Mol. Ther. 1 (1999), 487-492.

As mentioned before, the methods of the present invention preferably employ eukaryotic cells, preferably mammalian cells, which have been genetically engineered to express an ETT polypeptide or a functional fragment thereof. Preferably, in particular if a stably transfected cell line is desired to be established, the expression of the ETT polypeptide should be inducible, for example by using an inducible eukaryotic expression system such as one of those described above or used in the appended Example 1. In addition, or alternatively, the cells employed in the method of the present invention may be genetically engineered to suppress the expression of the endogenous ETT gene. This embodiment is particularly suited for the investigation of allelic variants of ETT and investigation of functional analogs and derivatives of wild-type ETT.

It may be optimal to use host cells that are capable of glycosylating ETT, typically including mammalian cells such as embryonic kidney 293 cells, COS cells, CHO, BHK-21 cells and the like. *Xenopus* oocytes are also suitable for expression of ETT RNA. In addition, host cells that have been used heretofore to express anion and in particular cation transporter polypeptides in recombinant cell culture are suitable. The host-vector system should yield substantially homogeneous ETT, thereby avoiding the need to purify various ETT alleles, isoforms or cleavage products from one another. If the host cell is capable of glycosylation, essentially all of the ETT molecules should be glycosylated. The term "cell" refers to at least one cell, but includes a plurality of cells appropriate for the sensitivity of the detection method. Cells suitable for the present invention may be yeast, or preferably eukaryotic, most preferably mammalian, see also supra.

The method of the present invention involves contacting a cell which expresses an ETT polypeptide as described above with a compound to be screened and determining if the level of the substrate, e.g. ergothioneine transport, is altered.

The amount of time necessary for cellular contact with the compound is empirically determined, for example, by running a time course with a known modulator and measuring cellular changes as a function of time; see also the Examples. The measurement means of the method of the present invention can be further defined by comparing a cell that has been exposed to a compound to an identical cell that has not been similarly expose to the compound. Alternatively two cells, one containing a functional ETT gene and a second cell identical to the first, but lacking a functional ETT gene, could be both be contacted with the same compound and compared for differences between the two cells. This technique is also useful in establishing the background noise of these assays. One of average skill in the art will appreciate that these control mechanisms also allow easy selection of cellular changes that are responsive to modulation of the functional ETT gene or gene product.

The cell that is contacted with the test substance can be derived from a single cell or a multi-cellular organism. Said multi-cellular organism can be selected from the group consisting of a vertebrate animal, a mammal, a primate, an invertebrate animal, an insect and a plant. The above described cells can also be comprised in a tissue or organism, i.e. non-human animal. General methods for the screening of compounds that have a desired effect on a cell or organism as measured in a specific assay are described in the prior art; see for example U.S. Pat. No. 6,165,709 and references cited herein. Cells, non-human animals and target gene expression and/or knock out systems can be found in the prior art and adapted for the method of the present invention; see for example the documents cited herein.

In one preferred embodiment of the method of the present invention, said cell, tissue or non-human animal is a transgenic cell, tissue or non-human animal which displays a substantially reduced or enhanced level of ETT gene expression and/or ETT activity compared to a corresponding wild-type animal. Usually, said transgenic non-human animal displaying a reduced level of ETT gene activity comprises at least one mutant allele of the ETT gene or a corresponding trans-dominant allele of a different ETT gene. Preferably, said transgenic non-human animal is a knock-out animal.

Preferably said substantially reduced or enhanced level of ETT gene expression and/or ETT activity results in an altered and a phenotypic response, i.e. an altered level of ergothioneine in the cell or plasma of the transgenic non-human animal. An agonist/activator or antagonist/inhibitor will then be identified by observing whether a candidate compound is able at a certain concentration to revert the phenotypic response of said transgenic non-human animal back to normal. In a particularly preferred embodiment, said transgenic non-human animal displays disorders as further described below.

The above described methods can also be adapted to identify ETT activating or co-stimulating compounds or for identifying inhibitors of ETT activity and stimulation comprising
(a) culturing a cell modified to express ETT and, optionally, in the presence of ergothioneine or a corresponding substrate of ETT; and optionally
(b) detecting the presence or absence of a signal generated from the interaction of the compound with the cells.

Thus, in case the test compound leads to signal identifying a decrease of ETT activity, said compound may be used for the treatment of diseases which are due to an increased level of ergothioneine in the cell. Likewise, if the signal indicates that ETT activity is enhanced in the presence of the test compound, said compound may be used for the treatment for disorders that are due to or associated with a reduced level of ergothioneine in the cell or the lack of it.

In one embodiment, the present invention relates to a method for identifying and/or obtaining a compound for treating a disease related to the immune system, which method comprises:
(a) providing a transgenic animal or a mutant animal, which animal expresses a variant ETT gene, due to which cells or tissue of said animal display a reduced level of ergothioneine compared to cells or tissue of a corresponding wild type or control animal;
(b) contacting the animal with a test compound; and
(c) detecting an improvement in a condition of the animal in response to the test compound, wherein the condition is a symptom of a disorder of the immune system.

Preferably, said animal is a mammal. A method for the production of a transgenic non-human animal, which is also encompassed by the present invention, for example transgenic mouse, comprises introduction of a polynucleotide or targeting vector encoding said polypeptide into a germ cell, an embryonic cell, stem cell or an egg or a cell derived therefrom. The non-human animal can be used in accordance with a screening method of the invention described herein. Production of transgenic embryos and screening of those can be performed, e.g., as described by A. L. Joyner Ed., Gene Targeting, A Practical Approach (1993), Oxford University Press. A general method for making transgenic non-human animals is described in the art, see for example WO94/24274. For making transgenic non-human organisms (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62 (1990), 1073-1085) essentially as described (Robertson, E. J. (1987) in Teratocarcinomas and Embryonic Stem Cells: A Practical Approach. E. J. Robertson, ed. (Oxford: IRL Press), 71-112) may be used for homologous gene targeting. Other suitable ES lines include, but are not limited to, the E14 line (Hooper et al., Nature 326 (1987), 292-295), the D3 line (Doetschman et al., J. Embryol. Exp. Morph. 87 (1985), 27-45), the CCE line (Robertson et al., Nature 323 (1986), 445-448), the AK-7 line (Zhuang et al., Cell 77 (1994), 875-884). The success of generating a mouse line from ES cells bearing a specific targeted mutation depends on the pluripotence of the ES cells (i.e., their ability, once injected into a host developing embryo, such as a blastocyst or morula, to participate in embryogenesis and contribute to the germ cells of the resulting animal). The blastocysts containing the injected ES cells are allowed to develop in the uteri of pseudopregnant nonhuman females and are born as chimeric mice. The resultant transgenic mice are chimeric for cells having either the recombinase or reporter loci and are backcrossed and screened for the presence of the correctly targeted transgene(s) by PCR or Southern blot analysis on tail biopsy DNA of offspring so as to identify transgenic mice heterozygous for either the recombinase or reporter locus/loci.

Effective generation of transgenic pigs and mice are also described; see Chang et al., BMC Biotechnol. 2 (1):5 (2002). Generation of transgenic rabbits is described in James et al., J. Mol. Cell. Cardiol. 34 (2002), 873-882 and Murakami et al., Theriogenology 57 (2002), 2237-2245. Furthermore, the generation of transgenic sheep is described for example in Kadokawa et al., Domest. Anim. Endocrinol. 24 (2003), 219-229 and Campbell, Methods Mol. Biol. 180 (2002), 289-301. U.S. Pat. No. 5,639,457 is also incorporated herein by reference to supplement the present teaching regarding transgenic pig and rabbit production. U.S. Pat. Nos. 5,175,384; 5,175,385; 5,530,179, 5,625,125, 5,612,486 and 5,565,186 are also each incorporated herein by reference to similarly supplement the present teaching regarding transgenic mouse and rat production.

Methods for producing transgenic flies, such as *Drosophila melanogaster* are also described in the art, see for example U.S. Pat. No. 4,670,388, Brand and Perrimon, Development 118 (1993), 401-415; and Phelps and Brand, Methods 14 (1998), 367-379. Transgenic worms such as *C. elegans* can be generated as described in Mello et al., Embo J. 10 (1991), 3959-3970; Plasterk, Methods Cell. Biol. 48 (1995), 59-80.

Preferably, the transgenic non-human animal comprises at least one inactivated or suppressed wild type allele of the ETT; see supra. This embodiment allows for example the study of the interaction of various mutant forms of these genes or gene products on the onset of the clinical symptoms and/or may be used to verify the involvement of said gene(s) in the disorder to be studied. All the applications that have been herein before discussed with regard to a transgenic animal also apply to animals carrying two, three or more transgenes. It might be also desirable to inactivate ETT gene expression or function at a certain stage of development and/or life of the transgenic animal. This can be achieved by using, for example, tissue specific, developmental and/or cell regulated and/or inducible promoters which drive the expression of, e.g., an antisense or ribozyme directed against the RNA transcript encoding the target gene mRNA; see also supra. A suitable inducible system is for example tetracycline-regulated gene expression as described, e.g., by Gossen and Bujard (Proc. Natl. Acad. Sci. 89 USA (1992), 5547-5551) and Gossen et al. (Trends Biotech. 12 (1994), 58-62); see also supra. Similar, the expression of a mutant target gene may be controlled by such regulatory elements. Preferably, the presence of the transgenes in cells of the transgenic animals leads to various physiological, developmental and/or morphological changes, preferably to conditions related to disorders of the immune system, CNS and/or eye such as those described herein. In another embodiment, said transgenic non-human animal is used for a process in the discovery of drugs for the treatment of a disorder of the immune system. In particular, mammalian animals are preferred, especially mice and rats.

The assay methods of the present invention can be in conventional laboratory format or adapted for high throughput. The term "high throughput" (HTS) refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired. Examples of assay formats include 96-well, 384-well or more-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

The test substances which can be tested and identified according to a method of the invention may be expression libraries, e.g., cDNA expression libraries, peptides, proteins, nucleic acids, antibodies, small organic compounds, hormones, peptidomimetics, PNAs, aptamers or the like (Milner, Nature Medicine 1 (1995), 879-880; Hupp, Cell 83 (1995), 237-245; Gibbs, Cell 79 (1994), 193-198 and references cited supra). The test substances to be tested also can be so called "fast seconds" of known drugs. The invention also relates to further contacting the test cells with a second test substance or mixture of test substances in the presence of the first test substance.

In the method of the invention, said cells are preferably contained in a container, for example in a well in a microtiter plate, which may be a 24, 96, 384 or 1586 well plate. Alternatively, the cells can be introduced into a microfluidics device, such as those provided by Caliper (Newton, Mass., USA). In another preferred embodiment, step (b) of the method of the present invention comprises taking 2, 3, 4, 5, 7, 10 or more measurements, optionally at different positions within the container. In some embodiments of the method of the present invention, a compound known to activate or inhibit the target gene or gene product is added to the medium prior to step (b).

Preferably, in a first screen said test substance is comprised in and subjected as a collection of compounds. Said collection of compounds may have a diversity of about $10^3$ to about $10^5$. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Drug discovery by dynamic combinatorial libraries is described, for example, in Nat. Rev. Drug Discov. 1 (2002), 26-36 and Drug Discov. Today 7 (2002), 117-125.

Furthermore, the above described methods can, of course, be combined with one or more steps of any of the above described screening methods or other screening methods well known in the art. Methods for clinical compound discovery comprises for example ultrahigh-throughput screening (Sundberg, Curr. Opin. Biotechnol. 11 (2000), 47-53) for lead identification, and structure-based drug design (Verlinde and Hol, Structure 2 (1994), 577-587) and combinatorial chemistry (Salemme et al., Structure 15 (1997), 319-324) for lead optimization. Once a drug has been selected, the method can have the additional step of repeating the method used to perform rational drug design using the modified drug and to assess whether said modified drug displays better affinity according to for example interaction/energy analysis. The method of the present invention may be repeated one or more times such that the diversity of said collection of compounds is successively reduced.

In a further aspect the present invention also relates to a method of determining the toxicity of a compound comprising the steps of any one of the methods described hereinbefore, wherein a reduced or enhanced level or activity of the ETT is indicative for the toxicity of the compound. This embodiment is based on the observation that a given compound such as a household chemical, nutrition, feed or food additive, cosmetic, pharmaceutical, etc. may have the undesired side effect of modulating the ergothioneine transporter, thereby possibly damaging the cell. Likewise, due to its modulating effect on ETT, a given compound may give rise to allergic reactions of the animal body, in particular of humans.

In order to identify such compounds and optionally modify them in order to reduce their activity on ETT, the methods described herein can be specifically employed. Furthermore, it is possible to establish a profile of a given compound with respect to its activity on the ETT, with the ETT as the sole target for its use in a set of targets to be assessed and used for establishing the profile. For such embodiments the use of array technology is particularly envisaged. For example, Zhang et al., J. Pharmacol. Exp. Ther. 286 (1998), 354-361, describe the functional characterization of the organic cation transporter (HOCT1) in a transiently transfected human cell line (HeLa) on an array of organic cations and other compounds. Such system can of course easily be adapted in accordance with the present invention, for example with corresponding cells stably transfected with ETT plasmid DNA tested on an array of test compounds including substrate ergothioneine. The mentioned array technology can of course also be used for identifying and obtaining agonists and antagonists that are useful as drugs for the treatment of disorders such as those arising from cell damage due to oxidative stress or autoimmune diseases, in particular rheumatoid arthritis.

Furthermore, the present invention relates to the use of a compound identified, isolated and/or produced by any of these methods for obtaining and manufacturing a drug. Usually, an enhanced or reduced level or activity of the ETT transporter is indicative for the drug. Compounds identified, isolated and/or produced by the method described above can also be used as lead compounds in drug discovery and preparation of drugs or prodrugs. This usually involves modifying the lead compound or a derivative thereof or an isolated compound so as to achieve (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmakinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carbon acids, or (iii) esterification of hydroxyl groups to, e.g. phosphates, pyrophosphates or sulfates or hemi succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiff's bases, oximes, acetales, ketales, enolesters, oxazolidines, thiozolidines or combinations thereof; and (b) formulating the product of said modification with a pharmaceutically acceptable carrier.

The various steps recited above are generally known in the art. For example, computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, peptide mimetics and/or computer aided design of appropriate derivatives and analogues can be used, for example, according to the methods described above. Methods for the lead generation in drug discovery also include using proteins and detection methods such as mass spectrometry (Cheng et al. J. Am. Chem. Soc. 117 (1995), 8859-8860) and some nuclear magnetic resonance (NMR) methods (Fejzo et al., Chem. Biol. 6 (1999), 755-769; Lin et al., J. Org. Chem. 62 (1997), 8930-8931). They may also include or rely on quantitative structure-action relationship (QSAR) analyses (Kubinyi, J. Med. Chem. 41 (1993), 2553-2564, Kubinyi, Pharm. Unserer Zeit 23 (1994), 281-290) combinatorial biochemistry, classical chemistry and others (see, for example, Holzgrabe and Bechtold, Pharm. Acta Helv. 74 (2000), 149-155). Furthermore, examples of carriers and methods of formulation may be found in Remington's Pharmaceutical Sciences.

The ETT transporter protein of this invention can be used to control internal absorption and dynamics of drugs. Based on the results of detailed analysis of the substrate specificity of ETT, drugs can be designed so as to be transported by this transporter and absorbability of the drugs mediated by ETT can be improved. Conventional modifications to enhance hydrophobicity are no longer necessary for drugs so designed, which enables speedily and efficiently developing water-soluble drugs that are easy to handle. The drugs thus developed are thought to be absorbed principally depending on the internal distribution pattern of ETT, and an organ-specific delivery of the drugs thus becomes possible. Especially, if the ETT is distributed in the target organ of a drug, an ideal drug delivery system (DDS) can be developed. If a drug is to be absorbed mediated by not the ETT but other transporters, the drug can be designed so as to be specific to other transporter proteins by designing it considering the substrate specificity of the ETT. Since the ETT is also present in the kidney, it is possible to reduce the nephrotoxicity produced by a drug by designing the drug so that it can be readily excreted by the ETT.

Once a drug has been selected in accordance with any one of the above described methods of the present invention, the drug or a pro-drug thereof can be synthesized in a therapeutically effective amount. As used herein, the term "therapeutically effective amount" means the total amount of the drug or pro-drug that is sufficient to show a meaningful patient benefit, i.e. treatment, healing, prevention or amelioration of a condition related to disorders related to a low or high level of ergothioneine in the cell or an increase in rate of treatment, healing, prevention or amelioration of such conditions. In addition or alternatively, in particular with respect to pre-clinical testing of the drug the term "therapeutically effective amount" includes the total amount of the drug or pro-drug that is sufficient to elicit a physiological response in a non-human animal test.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

The compositions of the invention may be administered locally or systemically e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as interleukins or interferons depending on the intended use of the pharmaceutical composition.

In accordance with the present invention the pharmaceutical compositions are administered to a subject in an effective dose of between about 0.1 µg to about 10 mg units/day and/or units/kg body weight; see also infra.

The dosage regimen of the pharmaceutical compositions in all of the above described methods and uses of the present invention will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 µg to 10 mg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 0.01 µg to 10 mg units per day. If the regimen is a continuous infusion, it should also be in the range of 0.01 µg to 10 mg units per kilogram of body weight per minute, respectively. Progress can be monitored by periodic assessment. Dosages will vary but a preferred dosage for intravenous administration of nucleics acids is from approximately $10^6$ to $10^{12}$ copies of the nucleic acid molecule.

Therapeutic or diagnostic compositions of the invention are administered to an individual in an effective dose sufficient to treat or diagnose disorders in which modulation of an ETT gene or ETT activity is indicated. The effective amount may vary according to a variety of factors such as the individual's condition, weight, sex and age. Other factors include the mode of administration. The pharmaceutical compositions may be provided to the individual by a variety of routes such as by intracoronary, intraperitoneal, subcutaneous, intravenous, transdermal, intrasynovial, intramuscular or oral routes. In addition, co-administration or sequential administration of other agents may be desirable.

As already explained further above, one aspect of the present invention is based on the finding that cells of the immune systems such as monocytes and macrophages appeared to be responsive to the intracellular ergothioneine level, which in turn opens up a new medical treatment of diseases that are related to disorders of the immune system, for example due to autoaggressive macrophages. Thus, in one particular aspect, the present invention relates to the use of a compound which enhances ergothioneine transport activity of an ETT polypeptide, of ergothioneine or a derivative or analog thereof, an ETT polypeptide or functional fragment thereof, a nucleic acid molecule encoding said ETT polypeptide or functional fragment thereof, or of a compound identified according to a method of the present invention for the manufacture of a medicament for the treatment and/or prophylaxis of a disease related to the immune system.

Autoimmune diseases are complex diseases in which both genetic and environmental factors are involved. Excessive oxidative stress is thought to have an important role in the pathogenesis of autoimmune diseases by enhancing the inflammation, inducing apoptotic cell death, and breaking down the immunological tolerance. When the state of oxidative stress was investigated in patients with rheumatoid arthritis (RA), systemic lupus erythematosus (SLE), and Sjogren's syndrome (SS) by oxidative stress profile (OSP), most subjects were in excessive oxidative stress or in defective antioxidant potentials; see, e.g., Kumagai et al., Rinsho Byori 51 (2003), 126-132. Hence, extensive evidence supports oxidative stress via endogenous and exogenous agents as an important factor in induction of autoimmunity. Oxidative stress arises from the immune system and other endogenous sources. The literature contains support for oxidative stress involvement of various drugs and other exogenous substances that produce the condition. Studies reveal prevention or amelioration by antioxidants; for review see, e.g., Kovacic and Jacintho, Mini Rev. Med. Chem. 3 (2003), 568-575.

For the above reasons, one particular disease to be treated in accordance with the present invention is an autoimmune disease, for example an autoimmune disease selected from the group consisting of autoimmune hemolytic anemia, autoimmune thrombocytopenic purpura, Goodpasture's syndrome, pemphigus vulgaris, acute rheumatic fever, mixed essential cryoglobulinemia, systemic lupus erythematosus, rheumatoid arthritis, insulin-dependent diabetes mellitus, experimental autoimmune encephalomyelitis (EAE), multiple sclerosis, thyroid diseases including Hashimotos's thyroiditis and Graves's diseases, primary Sjögren's syndrome, primary biliary cirrhosis, myasthenia gravis.

The concentration of ergothioneine in human and mammalian tissue has been estimated to be 1-2 mM, which suggests that ergothioneine may serve as a non-toxic thiol buffering antioxidant in vivo and may find applications in pharmaceutical preparations where oxidative stability, i.e. protection against oxidative damage and cell death is desired; see, e.g., Aruoma et al., Food Chem. Toxicol. 37 (1999), 1043-1053; for a general review of intracellular antioxidants see Chaudiere and Ferrari-Iliou, Food. Chem. Toxicol. 37 (1999), 949-962. Furthermore, it has been recently found that ergothioneine rescues PC12 cells from β-amyloid-induced apoptotic cell death, demonstrating the importance of diet-derived antioxidants in the management of Alzheimer's Disease and other neurodegenerative disorders; see Jang et al., Free Radic. Biol. Med. 36 (2004), 288-299.

Mitochondria are subcellular organelles present in all oxygen-utilizing organisms in which energy in the form of adenosine triphosphate (ATP) is generated, and oxygen in reduced to water. Ninety percent of the oxygen taken in is consumed in mitochondria. A substantial byproduct of this ATP generation is the formation of potentially toxic oxygen radicals. For example, it is estimated that 1-2% of all reduced oxygen yields superoxide and hydrogen peroxide. Other reactive oxygen species (ROS) of that form are singlet oxygen and hydroxyl radical. Under stress conditions in the cell this can rise to 10% of all consumed oxygen. Mitochondrial membranes are sensitive to lipid peroxidation and depolarization resulting from these ROS. Mitochondrial damage is also a result of exposure to sunlight, which forms ROS as indicated above. Because damage to mitochondria is believed to be the cause or an important factor in some diseases, such as cancer, diabetes, cataract, neurodegenerative disease, porphyrias, cardiovascular disease, and also a contributor to the complications of aging, a method of protecting mitochondria from such damage, repairing such damage, is desired. Cellular damage from burns to the skin and lungs from contact with or exposure to fire and other sources of intense heat is mediated through radical damage. Furthermore, exposure to adverse environmental factors, including industrial air pollutants and petroleum and tobacco combustion products, may contribute to oxidative damage to pulmonary and other tissues of the body. In addition, various therapeutic regimens such as chemotherapeutic drugs and radiation therapy for the treatment of dysproliferative diseases induce significant oxidant-stress-related side effects, such as cardiotoxicity. The present invention relates to applied agents which protect the mitochondria from such damage.

Thus, in a still further aspect, the present invention relates to the use of a compound which enhances ergothioneine transport activity of an ETT polypeptide, an ETT polypeptide or functional fragment thereof, a nucleic acid molecule encoding said ETT polypeptide or functional fragment thereof, or of a compound identified according to the method of the present invention for the manufacture of a pharmaceutical composition for the treatment or amelioration of a disease arising from damage to mitochondria caused by radiation, radicals and reactive oxygen species.

In one embodiment, said damage results from exposure to airborne toxins selected from the group consisting of tobacco combustion products, industrial pollutants, petroleum combustion products, ozone, nitric oxide, radioactive particulates, and combinations thereof.

In another embodiment, said damage results from exposure to the group consisting of ultraviolet radiation, solar radiation, suntanning radiation, thermal radiation, sunburning radiation, gamma radiation, microwave radiation, electromagnetic radiation, nuclear radiation, and combinations thereof.

In a still further embodiment, said damage is pathologically causative in a disease or condition selected from the group consisting of cataract, macular degeneration, degenerative retinal damage, lung cancer, skin cancer, melanoma, sunburn, radiation poisoning, asbestosis, atherosclerosis, Parkinson's Disease, Alzheimer's Disease, muscular dystrophy, multiple sclerosis, burns, emphysema, bronchopulmonary dysphasia, iron overload diseases, inflammation, hemochromatosis, thalassemia, pancreatitis, diabetes, autoimmune nephrotic syndrome, heavy metal-induced nephrotoxicity, and radiation injury.

In another embodiment, said damage is induced by the exposure to or consumption of nuclear waste, fallout, industrial chemicals or ethanol.

In view of the findings of the present invention and the theory that ergothioneine serves as a buffering antioxidant in vivo it is also conceived in accordance with the present invention that the controlled depletion of ergothioneine inside the cell may have therapeutic use. For example, it is known that oxidative stress can trigger apoptosis, or cause necrosis depending upon the dose and the exposure time of the oxidizing agent. Accordingly, oxidative stress can also be used to induce cell death, which may be of particular advantage for the treatment of tumors since oxidative stress-induced cell death is known to surpass cancer cellular defense systems such as for example mutations in the tumor suppressor p53 or overexpression of members of the bcl-2 family of proteins. In view of the above, the present invention also contemplates the therapeutic strategy to mediate depletion of ergothioneine in a target cell in order to induce cell death. More particularly, the present invention relates to the use of a compound capable of modulating the ergothioneine transport activity or expression of an ETT for the manufacture of a pharmaceutical composition for inducing cell death, preferably in the course of cancer treatment. In this context, it has been shown that malignant cells in general are more active than normal cells in the production of reactive oxygen species, are under intrinsic oxidative stress, and thus are more vulnerable to damage by agents generating reactive oxygen species (ROS) such as 2-metoxyestradiol (2-ME); see for example Hilemann et al., Cancer Chemother. Pharmacol. 53 (2004), 209-219. Accordingly, the present invention envisages a therapeutic application of compounds which lead to a decrease level of intracellular ergothioneine in cancer treatment, for example as an adjuvant cancer therapy which may be introduced into human cancer therapy without any change in the classical anti-cancer protocols and without any supplementary risk for patients. Thus, a compound acting on ETT may be administered either alone or preferably in combination with classical anti-cancer agents. In principle, any malignant cell may be treated, for example carcinomas of the lung, colorectum, pancreas, larynx, stomach, peripheral and central nervous system, other carcinomas, sarcomas, chronic myeloic leukemia (CML), acute myeloic leukemia (AML), acute lymphatic leukemia (ALL), non Hodgin Lymphoma (NHL), myeloproliferative syndrome (MPS), myelodysplastic syndrome (MDS), plasmocytoma, or other leukemias.

Compounds that may be used for this embodiment of the invention may be anyone of the above described antagonists, antisense oligonucleotides, siRNA, anti-ETT antibodies, and the like.

Within the above described medical treatments, said pharmaceutical composition can be designed to be co-administered with a therapeutic agent or radiation treatment, said therapeutic agent may be selected from the group consisting of anti-cancer agents, anti-cancer radiation therapy, fibrinolytic therapy, and combinations thereof.

The potential of compounds capable of modulating ETT transporter activity to protect a mammal from mitochondrial damage and the level of compound, if necessary in combination with ergothioneine necessary to afford protection may be assessed in vitro exposing aliquots of a cellular sample from said mammal to the damaging agent or condition, said aliquots containing various concentrations of the compound, and optionally ergothioneine, that latter preferably at a constant level. The damage to the mitochondria of the various aliquots is determined, as well as the lowest concentration, if any, of the compound providing sufficient protection from damage. Appropriate assay systems can be employed in accordance with the present invention, for example an experimental example with mouse keratinocytes is described in international application WO98/36748. Furthermore, pharmaceutical formulations are described that may be equally applied to the compounds capable of modulating ETT, and identified in accordance with a method of the present invention described hereinbefore.

Moncaster et al., Neurosci. Lett. 328 (2002), 55-59, describe that ergothioneine appears to be neuroprotective in an vivo rat retinal model and suggest that antioxidants may provide a useful means of modulating glutamate-based toxicity. Furthermore, international application WO03/082216 describes the neuroprotective effects of ergothioneine, in particular on the mammalian central nervous system (CNS) cell from damage due to, for example, the exposure of the cell to a neurotoxic compound, such as glutamate or a glutamate analog. Other neurotoxic compounds may include certain anti-cancer compounds, or free radicals and oxidants such as those described above. Likewise, it is suggested that supply of ergothioneine may be used for treatment and amelioration of neurodegeneration accompanying disease conditions such as Alzheimer's Disease, multiple sclerosis, Down's syndrome, amyotropic lateral sclerosis, Parkinson's Disease, traumatic injury including brain and spinal cord injury, macular degeneration, HIV/AIDS and optic neuropathies and retinopathies.

Furthermore, reactive oxygen species (ROS) are implicated in the pathophysiology of diseases of the eye. For example, Shires et al., Comp. Biochem. Physiol. C. Pharmacol. Toxicol. Endocrinol. 117 (1997), 117-120 (S1367-8280), provided results on ergothioneine distribution in bovine and porcine ocular tissues, which are consistent with a role for ergothioneine in prevention of oxidative damage to the eye. In accordance with the present invention a significant accumulation of ergothioneine in the lens of the eye could be found. Therefore, in the eye, cataract, macular degeneration and degenerative retinal damage may be treated for example with topical, oral or parentally-administered compound of the present invention, optionally in combination with ergothioneine.

Hence, in a still further embodiment the present invention relates to the use of a compound which enhances ergothioneine transport activity of an ETT polypeptide, an ETT polypeptide or functional fragment thereof, a nucleic acid molecule encoding said ETT polypeptide or functional fragment thereof, or of a compound identified according to the method of the present invention for the manufacture of a pharmaceutical composition for protecting, treating or ameliorating a mammalian central nervous system (CNS) cell from damage and/or of a disease of the eye such as cataract.

As mentioned before, the damage may result from exposure to an oxidant, a cytokine or a neurotoxic compound. Said neurotoxic compound may be selected from the group consisting of glutamate, a glutamate analog, and an anticancer compound.

On the other hand, the damage may result from the presence of a neurodegenerative disease, such as Alzheimer's Disease, multiple sclerosis, Down's syndrome, amyotropic lateral sclerosis, Parkinson's Disease, traumatic brain injury, acute and chronic spinal cord injury, macular degeneration, HIV/AIDS, optic neuropathy or retinopathy.

Methods for determining an appropriate amount of the compound capable of modulating, preferably enhancing the expression and/or activity of ETT sufficient to ameliorate or prevent the onset or progression of any one of the above described disorders can be done, for example, according to the assays described in WO03/082216, such as the described in vivo rat retinal model. In addition, this international application provides ample description for pharmaceutical compositions that may be applied to the ETT-specific compound, either alone or optionally in addition to ergothioneine or other anti-oxidants known to the person skilled in the art. Furthermore, it is immediately evident that the above described screening methods of the present invention are also intended to employ the animal models described for the investigation of ergothioneine, for example for its therapeutic use in conditions such as Parkinson's Disease in the unilateral 6-hydroxydopamine (6-OHDA) lesion rat model.

Guijarro et al., Food Chem. Toxicol. 40 (2002), 1751-1755, describe that inhibition of the glucose-mediated free radical dependent embryo malformation by ergothioneine is an important antioxidant prophylactic mechanism, which when combined with vitamin E could benefit the management of diabetic embryopathy.

In view of this finding, the present invention also relates to the use of a compound which enhances ergothioneine transport activity of an ETT polypeptide, an ETT polypeptide or functional fragment thereof, a nucleic acid molecule encoding said ETT polypeptide or functional fragment thereof, or of a compound identified according to a method of the present invention for the manufacture of a pharmaceutical composition for reducing the incidence of diabetes-associated embryopathy.

Methods for further screening the compounds described hereinbefore inasmuch they are capable of protecting a mammalian embryo from diabetes-associated embryopathy, either alone or in combination with other antioxidants are described, for example, in WO03/099277.

In addition, Rahman et al., Biochem. Biophys. Res. Commun. 302 (2003), 860-864, described that ergothioneine inhibits oxidative stress- and TNF-alpha-induced NF-kappa B activation and interleukin-8 release in alveolar epithelial cells and suggest molecular mechanism for the anti-inflammatory effects of ergothioneine. Thus, ETT-modulating compounds may also be used for the treatment of an inflammatory disease, for example Inflammatory Bowel Diseases (IBD) which include Crohn's Disease, indeterminate colitis (IC) and Ulcerative Colitis (UC).

The present invention also provides pharmaceutical compositions for the above described uses of the present invention. Such compositions comprise a therapeutically effective amount of a compound which modulates ergothioneine transport activity of an ETT polypeptide, an ETT polypeptide or functional fragment thereof, a nucleic acid molecule encoding said ETT polypeptide or functional fragment thereof, or of a compound identified according to the method of the present invention, and optionally ergothioneine as well, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents.

These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Administration of any one of the above described compounds, and optionally ergothioneine to the site of injury, the target cells, tissues, or organs, may be by way of oral administration as a pill or capsule or a liquid formulation or suspension. It may be administered via the transmucosal, sublingual, nasal, rectal or transdermal route.

Parenteral administration may also be via intravenous injection, or intraarterial, intramuscular, intradermal, subcutaneous, intraperitoneal, intraventricular, intrathecal and intracranial administration. For example, the composition of the present invention may be infused directly into a tissue or organ that had undergone an infarct, such as the brain or heart following a stroke or heart attack, in order to protect mitochondria in the cells of the ischemic penumbra, those outside of the immediate infarct zone which are not killed during the cessation of blood flow but undergo extensive ROS-mediated damage when blood flow is restored. Due to the nature of the neurological diseases or conditions for which the present invention is being considered, the route of administration may also involve delivery via suppositories. This is especially true in conditions such as stroke whereby the ability of the patient to swallow is compromised.

The mentioned compounds either alone or in combination with ergothioneine may be provided as a liposome formulation. Liposome delivery has been utilized as a pharmaceutical delivery system for other compounds for a variety of applications; see, for example Langer, Science 249 (1990), 1527-1533; Treat et al., (1989) in Liposomes in the Therapy of Infectious Disease and Cancer, Lopez-Berestein and Fidler (eds.), Liss: New York, pp. 353-365 (1989). Many suitable liposome formulations are known to the skilled artisan, and may be employed for the purposes of the present invention; see, for example, U.S. Pat. No. 5,190,762.

In a further aspect, compound liposomes can cross the blood-brain barrier, which would allow for intravenous or oral administration. Many strategies are available for crossing the blood-brain barrier, including but not limited to, increasing the hydrophobic nature of a molecule; introducing the molecule as a conjugate to a carrier, such as transferrin, targeted to a receptor in the blood-brain barrier; and the like. In another embodiment, the molecule can be administered intracranially or, more preferably, intraventricularly. In yet another embodiment, the compound can be administered in a liposome targeted to the blood-brain barrier.

Transdermal delivery of the compound, either as a liposome formulation or free compound, is also contemplated. Various and numerous methods are known in the art for transdermal administration of a drug, e.g., via a transdermal patch. It can be readily appreciated that a transdermal route of administration may be enhanced by use of a dermal penetration enhancer.

Controlled release oral formulations may be desirable when practicing the neuroprotective method of the invention.

The drug may be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects.

Pulmonary delivery of the compounds may be used for treatment as well. Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

Ophthalmic and nasal delivery of the above described compound, optionally in combination with ergothioneine may be used in accordance with the present invention. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextrins. For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Ophthalmic delivery of the compositions of the present invention is also contemplated for the protection and treatment of mitochondria, for example, in the lens of the eye, in which oxidative damage is believed to account for a high incidence of cataracts. Other ophthalmic uses include treatment or prophylaxis of macular degeneration and degenerative retinal damage. The compositions and formulations of the present invention are suited for the transmucosal delivery of the ETT modulators and optionally of ergothioneine. In particular, the compositions and formulations are particularly suited for sublingual, buccal or rectal delivery of agents that are sensitive to degradation by proteases present in gastric or other bodily fluids having enhanced enzymatic activity. Moreover, transmucosal delivery systems can be used for agents that have low oral bioavailability. The compositions of the instant invention comprise the compounds dissolved or dispersed in a carrier that comprises a solvent, an optional hydrogel, and an agent that enhances transport across the mucosal membrane. The solvent may be a non-toxic alcohol known in the art as being useful in such formulations of the present invention and may include, but not be limited to ethanol, isopropanol, stearyl alcohol, propylene glycol, polyethylene glycol, and other solvents having similar dissolution characteristics. Other such solvents known in the art can be found in The Handbook of Pharmaceutical Excipients, published by The American Pharmaceutical Association and The Pharmaceutical Society of Great Britain (1986) and the Handbook of Water-Soluble Gums and Resins, ed. By R. L. Davidson, McGraw-Hill Book Co., New York, N.Y. (1980).

Any transmucosal preparation suitable for administering the components of the present invention or a pharmaceutically acceptable salt thereof can be used. Particularly, the mixture is any preparation usable in oral, nasal, or rectal cavities that can be formulated using conventional techniques well known in the art. Preferred preparations are those usable in oral, nasal or rectal cavities. For example, the preparation can be a buccal tablet, a sublingual tablet, and the like preparation that dissolve or disintegrate, delivering drug into the mouth of the patient. A spray or drops can be used to deliver the drug to the nasal cavity. A suppository can be used to deliver the mixture to the rectal mucosa. The preparation may or may not deliver the drug in a sustained release fashion.

A specific embodiment for delivery of the components of the present invention is a mucoadhesive preparation. A mucoadhesive preparation is a preparation which upon contact with intact mucous membrane adheres to said mucous membrane for a sufficient time period to induce the desired therapeutic or nutritional effect. The preparation can be a semisolid composition as described, for example, in WO96/09829. It can be a tablet, a powder, a gel or film comprising a mucoadhesive matrix as described, for example, in WO96/30013. The mixture can be prepared as a syrup that adheres to the mucous membrane.

Suitable mucoadhesives include those well known in the art such as polyacrylic acids, preferably having the molecular weight between from about 450,000 to about 4,000,000, for example, Carbopol934P, sodium carboxymethylcellulose (NaCMC), hydroxypropylmethylcellulose (HPMC), or for example, Methocel™ K100, and hydroxypropylcellulose.

The delivery of the components of the present invention can also be accomplished using a bandage, patch, device and any similar devide that contains the components of the present invention and adheres to a mucosal surface. Suitable transmucosal patches are described for example in WO93/23011, and in U.S. Pat. No. 5,122,127, both of which are hereby incorporated by reference. The patch is designed to deliver the mixture in proportion to the size of the drug/mucosa interface. Accordingly, delivery rates can be adjusted by altering the size of the contact area. The patch that may be best suited for delivery of the components of the present invention may comprise a backing, such backing acting as a barrier for loss of the components of the present invention from the patch. The backing can be any of the conventional materials used in such patches including, but not limited to, polyethylene, ethyl-vinyl acetate copolymer, polyurethane and the like. In a patch that is made of a matrix that is not itself a mucoadhesive, the matrix containing the components of the present invention can be coupled with a mucoadhesive component (such as a mucoadhesive described above) so that the patch may be retained on the mucosal surface. Such patches can be prepared by methods well known to those skilled in the art.

Preparations usable according to the invention can contain other ingredients, such as fillers, lubricants, disintegrants, solubilizing vehicles, flavours, dyes and the like. It may be desirable in some instances to incorporate a mucous membrane penetration enhancer into the preparation. Suitable penetration enhancers include anionic surfactants (e.g. sodium lauryl sulphate, sodium dodecyl sulphate), cationic surfactants (e.g. palmitoyl DL camitine chloride, cetylpyridinium chloride), nonionic surfactants (e.g. polysorbate 80, polyoxyethylene 9-lauryl ether, glyceryl monolaurate, polyoxyalkylenes, polyoxyethylene 20 cetyl ether), lipids (e.g.

oleic acid), bile salts (e.g. sodium glycocholate, sodium taurocholate), and related compounds.

The administration of the compounds of the present invention can be alone, or in combination with other compounds effective at treating the various medical conditions contemplated by the present invention. Also, the compositions and formulations of the present invention, may be administered with a variety of analgesics, anesthetics, or anxiolytics to increase patient comfort during treatment.

The compositions of the invention described herein may be in the form of a liquid. The liquid may be delivered as a spray, a paste, a gel, or a liquid drop. The desired consistency is achieved by adding in one or more hydrogels, substances that absorb water to create materials with various viscosities. Hydrogels that are suitable for use are well known in the art, see, for example, Handbook of Pharmaceutical Excipients, published by The American Pharmaceutical Association and The Pharmaceutical Society of Great Britain (1986) and the Handbook of Water-Soluble Gums and Resins, ed. by R. L. Davidson, McGraw-Hill Book Co., New York, N.Y. (1980).

Suitable hydrogels for use in the compositions include, but are not limited to, hydroxypropyl cellulose, hydroxypropyl methyl cellulose, sodium carboxymethyl cellulose and polyacrylic acid. Preferred hydrogels are cellulose ethers such as hydroxyalkylcellulose. The concentration of the hydroxycellulose used in the composition is dependent upon the particular viscosity grade used and the viscosity desired in the final product. Numerous other hydrogels are known in the art and the skilled artisan could easily ascertain the most appropriate hydrogel suitable for use in the instant invention.

The mucosal transport enhancing agents useful with the present invention facilitate the transport of the agents in the claimed invention across the mucosal membrane and into the blood stream of the patient. The mucosal transport enhancing agents are also known in the art, as noted in U.S. Pat. No. 5,284,657, incorporated herein by reference. These agents may be selected from the group of essential or volatile oils, or from non-toxic, pharmaceutically acceptable inorganic and organic acids. The essential or volatile oils may include peppermint oil, spearmint oil, menthol, eucalyptus oil, cinnamon oil, ginger oil, fennel oil, dill oil, and the like. The suitable inorganic or organic acids useful for the instant invention include but are not limited to hydrochloric acid, phosphoric acid, aromatic and aliphatic monocarboxylic or dicarboxylic acids such as acetic acid, citric acid, lactic acid, oleic acid, linoleic acid, palmitic acid, benzoic acid, salicylic acid, and other acids having similar characteristics. The term "aromatic" acid means any acid having a 6-membered ring system characteristic of benzene, whereas the term "aliphatic" acid refers to any acid having a straight chain or branched chain saturated or unsaturated hydrocarbon backbone.

Other suitable transport enhancers include anionic surfactants (e.g. sodium lauryl sulfate, sodium dodecyl sulfate), cationic surfactants (e.g. palmitoyl DL camitine chloride, cetylpyridinium chloride), nonionic surfactants (e.g. polysorbate 80, polyoxyethylene 9-lauryl ether, glyceryl monolaurate, polyoxyalkylenes, polyoxyethylene 20 cetyl ether), lipids (e.g. oleic acid), bile salts (e.g. sodium glycocholate, sodium taurocholate), and related compounds.

When the compositions and formulations of the instant invention are to be administered to the oral mucosa, the preferred pH should be in the range of pH 3 to about pH 7, with any necessary adjustments made using pharmaceutically acceptable, non-toxic buffer systems generally known in the art.

For topical delivery, a solution of the compounds described hereinbefore either alone or in combination with ergothioneine in water, buffered aqueous solution or other pharmaceutically-acceptable carrier, or in a hydrogel lotion or cream, comprising an emulsion of an aqueous and hydrophobic phase, at a concentration of between 50 μM and 5 mM, is used. A preferred concentration is about 1 mM. To this may be added ascorbic acid or its salts, or other ingredients, or a combination of these, to make a cosmetically-acceptable formulation. Metals should be kept to a minimum. It may be preferably formulated by encapsulation into a liposome for oral, parenteral, or, preferably, topical administration.

The invention provides methods of treatment comprising administering to a subject a neuroprotectively effective amount of the above described compositions. In one embodiment, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In one specific embodiment, a non-human mammal is the subject. In another specific embodiment, a human mammal is the subject. The precise dose to be employed in the formulation will also depend on the route of administration, and the seriousness of the disease or disorder, and should be decided according to the judgment of the practitioner and each subject's circumstances. Effective doses may be extrapolated from dose-response curves derived from in vitro or animal model test systems.

The appropriate concentration of the therapeutic agent might be dependent on the particular agent. The therapeutically effective dose has to be compared with the toxic concentrations; the clearance rate as well as the metabolic products play a role as do the solubility and the formulation. Therapeutic efficacy and toxicity of compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Thus, as can be readily appreciated by one of ordinary skill in the art, the uses and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In one embodiment of the present invention, the compound to be used in the compositions is a nucleic acid molecule or encoded by a nucleic acid molecule and is designed for use in gene therapy. For those embodiments gene therapy intervention is also envisaged. In these embodiments, said nucleic acid molecules are preferably contained in a vector that can be an expression, a gene transfer or gene targeting vector. Gene therapy, which is based on introducing therapeutic genes into cells by ex-vivo or in-vivo techniques is one of the most important applications of gene transfer. Transgenic mice expressing a neutralizing antibody directed against nerve growth factor have been generated using the "neuroantibody" technique; Capsoni, Proc. Natl. Acad. Sci. USA 97 (2000), 6826-6831 and Biocca, Embo J. 9 (1990), 101-108. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Onodua, Blood 91 (1998), 30-36; Verzeletti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO94/29469; WO97/00957; U.S. Pat. No. 5,580,859; U.S. Pat. No. 5,589,466; U.S. Pat. No. 4,394,448 or Schaper, Current Opinion in Biotechnology 7 (1996), 635-640, and references cited therein. In particular, said vectors and/or gene delivery systems are also described in gene therapy approaches in neurological tissue/cells (see, inter alia Blömer, J. Virology 71 (1997) 6641-6649) or in the hypothalamus (see, inter alia, Geddes, Front Neuroendocrinol. 20 (1999), 296-316 or Geddes, Nat. Med. 3 (1997), 1402-1404). Further suitable gene therapy constructs for use in neurological cells/tissues are known in the art, for example in Meier, J. Neuropathol. Exp. Neurol. 58 (1999), 1099-1110. Preferred expression vectors for use in a therapeutic composition include any appropriate gene therapy vectors, such as nonviral (e.g., plasmid vectors), retroviral, adenoviral, herpes simplex viral, adeno-associated viral, polio viruses and vaccinia vectors. Multiple teachings of gene therapy are available for those skilled in the art, e.g., Anderson, Science 226 (1984), 401-409; Hughes, Current Communications in Molecular Biology 71 (1988), 1-12; Muzyczka and McLaughlin, Communications in Molecular Biology 70 (1988), 39-44; Friedman, Science 244 (1989), 1275-1281 and Anderson, Science 256 (1992), 608-613.

The nucleic acid molecule can be delivered "naked" by direct injection into the blood stream or to the desired tissue or organ of a subject. Alternatively, the vector can be combined with a lipid compound which facilitates the uptake of the molecule by cells. The lipid compound include liposome, lipofectins, cytofectins, lipid-based positive ions, and then introduced into the body fluids, the blood stream, or a selected tissue site. Liposome mediated gene therapy is well known in the art and is described by, e.g., Lesoon-Wood et al., Human Gene Ther. 6 (1995), 395; Tsan et al., Am. J. Physiol 268 (1995), 11052; Vieweg et al., Cancer Res. 5585 (1995), 2366; Trivedi et al., J. Neurochem. 64 (1995), 2230; Hickman et al., Human Gene Ther. 5 (1994), 1477; Westbrook et al., Human Mol. Genet. 3 (1994), 2005; Schmid et al., Z. Gastroenterol 32 (1994), 665; Hofland et al., Biochem. Biophys. Res. Commun. 207 (1995), 492; and Plautz et al., Ann. N.Y. Acad. Sci. 7168 (1994), 144. Other DNA carriers which can facilitate the uptake of a desired vector by the target cells include nuclear protein, or ligands for certain cell receptors, which can be combined with a vector in engineered vesicles for delivery. The introduction and gene therapeutic approach should, preferably, lead to the expression of a functional copy of the ETT gene of the invention. On the other hand, if ETT gene expression should be reduced, the expression of the introduced vector preferably leads to the production of an inhibitor as described above, for example antisense RNA or RNAi molecules.

In further embodiments, the above described compositions are administered as a dietary supplement. In a more specific embodiment, the dietary supplement is in the form of an oral capsule or tablet or a liquid suspension. Other embodiments include administration of the composition in a form suitable for sublingual or buccal delivery. Furthermore, the compositions may supplement other dietary compositions such as those containing ergothioneine. For example, Deiana et al., Clin Nutr (23) 2004, 183-193, described that supplementation with l-ergothioneine not only protects the organs kidney and liver against the lipid peroxidation but conserves the consumption of endogenous glutathione and alpha-tocopherol. Furthermore, the consumption of mushrooms is suggested as a better dietary sources of 1-ergothioneine to humans.

It will be apparent to the person skilled in the art that the use of a compound which enhances ergothioneine transport activity of an ETT polypeptide, an ETT polypeptide or functional fragment thereof, a nucleic acid molecule encoding said ETT polypeptide or functional fragment thereof, or of a compound identified according to a method of the present invention as an antioxidant may be used as a stand-alone therapy in any one of the above described disorders and conditions, or can be used in combination with other agents or regimens in prevention or attenuation of the onset or progression of the mentioned diseases and conditions.

In some embodiments of the invention, the composition may further comprise at least one or more antioxidants. Suitable antioxidants include coenzyme Q, vitamin E, vitamin C, pyruvate, melatonin, niacinamide, N-acetylcysteine, GSH, and nitrones. Preferably, at least one of said antioxidants is ergothioneine.

If combination preparations for therapeutic use in any one of the above described conditions are envisaged, said composition comprises ergothioneine preferably at a concentration in the range of 1 µM to 10 mM, most preferably at a concentration of about 1 mM.

As described above, the diagnosis of many disorders related to ergothioneine are not straight forward but hampered by the fact that the gene or genes underlying the given disease are not known. With the finding of the present invention that ETT is involved in the onset of or at least associated with disorders ergothioneine is involved in, a means is now provided for diagnosing those diseases. Hence, in a further embodiment, the present invention relates to a method of diagnosing a disorder as defined above in a subject comprising:

a) assaying a sample from a subject for ETT transcriptional activity or ETT protein or transporter activity; and b) determining the level of ETT protein or transporter activity, wherein an altered level compared to a control sample indicates the presence of the disorder.

In a still further embodiment the present invention relates to a method of diagnosing a disorder as defined above in a subject comprising determining a mutation in the nucleic acid molecule encoding ETT in a sample from a subject, wherein the presence of a mutation indicates presence of the disorder.

For example, if a sample of a subject suffering from a disease or suspected to have a predisposition for a disease has been determined to display an aberrant activity of ETT, the subject may be treated to modulate the activity of ETT in accordance with the present invention. Depending on whether a reduced or enhanced ETT activity has been determined the subject may be treated with ETT or a corresponding activator and inhibitor of ETT activity, respectively.

In one embodiment, the method of the present invention comprises determining a mutation or allelic variation in the polynucleotide sequence of the ETT gene or mRNA, wherein said mutation or allelic variation results in an altered level of ergothioneine transporter activity compared to a wild type sequence.

In these embodiments, the ETT nucleic acid molecules, (poly)peptide, antibodies or other detections means are preferably detectably labeled. A variety of techniques are available for labeling biomolecules, are well known to the person skilled in the art and are considered to be within the scope of the present invention. Such techniques are, e.g., described in Tijssen, "Practice and theory of enzyme immuno assays", Burden, R H and von Knippenburg (Eds), Volume 15 (1985), "Basic methods in molecular biology"; Davis L G, Dibmer M D; Battey Elsevier (1990), Mayer et al., (Eds) "Immunochemical methods in cell and molecular biology" Academic Press, London (1987), or in the series "Methods in Enzymology", Academic Press, Inc. There are many different labels and methods of labeling known to those of ordinary skill in the art. Commonly used labels comprise, inter alia, fluorochromes (like fluorescein, rhodamine, Texas Red, etc.), enzymes (like horse radish peroxidase, β-galactosidase, alkaline phosphatase), radioactive isotopes (like $^{32}P$ or $^{125}I$), biotin, digoxygenin, colloidal metals, chemi- or bioluminescent compounds (like dioxetanes, luminol or acridiniums). Labeling procedures, like covalent coupling of enzymes or biotinyl groups, iodinations, phosphorylations, biotinylations, random priming, nick-translations, tailing (using terminal transferases) are well known in the art. Detection methods comprise, but are not limited to, autoradiography, fluorescence microscopy, direct and indirect enzymatic reactions, etc.

In addition, the above described compounds etc. may be attached to a solid phase. Solid phases are known to those in the art and may comprise polystyrene beads, latex beads, magnetic beads, colloid metal particles, glass and/or silicon chips and surfaces, nitrocellulose strips, membranes, sheets, animal red blood cells, or red blood cell ghosts, duracytes and the walls of wells of a reaction tray, plastic tubes or other test tubes. Suitable methods of immobilizing nucleic acids, (poly) peptides, proteins, antibodies, etc. on solid phases include but are not limited to ionic, hydrophobic, covalent interactions and the like. The solid phase can retain one or more additional receptor(s) which has/have the ability to attract and immobilize the region as defined above. This receptor can comprise a charged substance that is oppositely charged with respect to the reagent itself or to a charged substance conjugated to the capture reagent or the receptor can be any specific binding partner which is immobilized upon (attached to) the solid phase and which is able to immobilize the reagent as defined above.

Commonly used detection assays can comprise radioisotopic or non-radioisotopic methods. These comprise, inter alia, RIA (Radioisotopic Assay) and IRMA (Immune Radioimmunometric Assay), EIA (Enzym Immuno Assay), ELISA (Enzyme Linked Immuno Assay), FIA (Fluorescent Immuno Assay), and CLIA (Chemioluminescent Immune Assay). Other detection methods that are used in the art are those that do not utilize tracer molecules. One prototype of these methods is the agglutination assay, based on the property of a given molecule to bridge at least two particles.

For diagnosis and quantification of (poly)peptides, polynucleotides, etc. in clinical and/or scientific specimens, a variety of immunological methods, as described above as well as molecular biological methods, like nucleic acid hybridization assays, PCR assays or DNA Enzyme Immunoassays (Mantero et al., Clinical Chemistry 37 (1991), 422-429) have been developed and are well known in the art. In this context, it should be noted that the nucleic acid molecules may also comprise PNAs, modified DNA analogs containing amide backbone linkages. Such PNAs are useful, inter alia, as probes for DNA/RNA hybridization.

The above described compositions may be used for methods for detecting expression of the ETT gene by detecting the presence of mRNA coding for a (poly)peptide which comprises, for example, obtaining mRNA from cells of a subject and contacting the mRNA so obtained with a probe/primer comprising a nucleic acid molecule capable of specifically hybridizing with the target gene under suitable hybridization conditions, and detecting the presence of mRNA hybridized to the probe/primer. Further diagnostic methods leading to the detection of nucleic acid molecules in a sample comprise, e.g., polymerase chain reaction (PCR), ligase chain reaction (LCR), Southern blotting in combination with nucleic acid hybridization, comparative genome hybridization (CGH) or representative difference analysis (RDA). These methods for assaying for the presence of nucleic acid molecules are known in the art and can be carried out without any undue experimentation.

Furthermore, the invention comprises methods of detecting the presence of ETT protein in a sample, for example, a cell sample, which comprises obtaining a cell sample from a subject, contacting said sample with one of the aforementioned antibodies under conditions permitting binding of the antibody to the protein, and detecting the presence of the antibody so bound, for example, using immuno assay techniques such as radioimmunoassay or enzymeimmunoassay. Furthermore, one skilled in the art may specifically detect and distinguish polypeptides which are functional ETT proteins from mutated forms which have lost or altered their activity by using an antibody which either specifically recognizes a (poly)peptide which has native activity but does not recognize an inactive form thereof or which specifically recognizes an inactive form but not the corresponding polypeptide having native activity.

The invention also encompasses a method for diagnosing in a subject a predisposition to a disorder of the immune system such as one of those described above associated with the expression of an ETT gene allele; see supra. The detectable markers of the present invention may be labeled with commonly employed radioactive labels, such as, for example, $^{32}P$ and $^{35}S$, although other labels such as biotin or mercury as well as those described above may be employed as well. Various methods well-known to the person skilled in the art may be used to label the detectable markers. For example, DNA sequences and RNA sequences may be labeled with $^{32}P$ or $^{35}S$ using the random primer method. Once a suitable detectable marker has been obtained, various methods well-known to the person skilled in the art may be employed for contacting the detectable marker with the sample of interest. For example, DNA-DNA, RNA-RNA and DNA-RNA hybridizations may be performed using standard procedures. Various methods for the detection of nucleic acids are well-known in the art, e.g., Southern and northern blotting, PCR, primer extension and the like. Suitable further DNA amplification techniques are known in the art and comprise, inter alia, Ligase Chain reaction, Strand Displacement Amplification, Nucleic Acid Sequence based Amplification (NASBA), or Q-beta replicase.

Furthermore, the mRNA, cRNA, cDNA or genomic DNA obtained from the subject may be sequenced to identify mutations which may be characteristic fingerprints of ETT gene mutations in ETT disorders such as described above associated with the expression of the target gene or mutated versions thereof. The present invention further comprises methods, wherein such a fingerprint may be generated by RFLPs or AFLP of DNA or RNA obtained from the subject, optionally the DNA or RNA may be amplified prior to analysis, the methods of which are well known in the art. RNA fingerprints may be performed by, for example, digesting an RNA sample obtained from the subject with a suitable RNA-Enzyme, for example RNase T1, RNase T2 or the like or a ribozyme and, for example, electrophoretically separating and detecting the RNA fragments on PAGE as described above. Preferably, hybridization (and subsequent washing) is effected under stringent conditions; see, e.g., Sambrook et al., loc. cit. and supra.

Furthermore, the present invention relates to a method as described above wherein said sample is or is derived from hair, blood, serum, sputum, feces or another body fluid. The sample to be analyzed may be treated such as to extract, inter alia, nucleic acid molecules, (poly)peptides, or antibodies.

The present invention also relates to kit compositions containing specific reagents such as those described herein-before. Kits containing ergothioneine or a derivative or analog thereof, an ETT polypeptide or functional fragment thereof, a nucleic acid molecule encoding said ETT polypeptide or functional fragment thereof, a sense or antisense molecule derived from said nucleic acid molecule, or an antibody specific for ETT polypeptide may be prepared. Such kits are used to detect for example DNA which hybridizes to DNA of the ETT gene or to detect the presence of protein or peptide fragments in a sample. Such characterization is useful for a variety of purposes including but not limited to forensic analyses, diagnostic applications, and epidemiological studies in accordance with the above described methods of the present invention. The recombinant ETT proteins, DNA molecules, RNA molecules and antibodies lend themselves to the formulation of kits suitable for the detection and typing of the ETT gene. Such a kit would typically comprise a compartmentalized carrier suitable to hold in close confinement at least one container. The carrier would further comprise reagents such as recombinant protein or antibodies suitable for detecting the expression or activity of the ETT gene or gene product, or vectors and cell lines for use in any one of the above described screening methods. The carrier may also contain a means for detection such as labeled antigen or enzyme substrates or the like.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Several documents are cited throughout the text of this specification. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The above disclosure generally describes the present invention. A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11, (2001), 98-107.

Example 1

Generation of a Cell Line Based on HEK 293 Cells that Expresses ETTh at a High Level after Induction with Doxycycline The cDNA of ETTh (EMBL/GenBank accession number Y09881) was inserted into the eukaryotic expression vector pcDNA5/FRT/TO (Invitrogen) to yield pcDNA5/FRT/TO/ETTh. This plasmid was cotransfected together with plasmid pOG44 by lipofection with Tfx-50 (Promega) into Flp-In T-REx 293 cells (Invitrogen; referred to as 293-FIT-NT in the remainder). After antibiotic selection with hygromycin B and blasticidin S, the surviving cells, used as a pool and designated as 293-FIT-ETTh, were assayed for ETT transcripts by Northern analysis. In the presence of 1 µg/ml doxycycline in the growth medium for 20-48 h to turn on transcription, the ETT mRNA was about 100-fold more abundant than in the off-state without doxycycline in the medium (FIG. 1). With the constitutive expression vector pcDNA3ETTh, it was not possible to generate stably transfected cells that produced ETTh mRNA. Apparently, the 293 cells do not tolerate constant high-level expression of ETTh. With GFP attached to the C-terminus of ETTh, constructed by direct linking of both open reading frames, it could be shown by fluorescence microscopy that the chimeric protein was expressed and sorted to the plasma membrane of transfected cells.

Example 2

Elucidation of a Substrate of ETT by LC-MS Difference Shading

The cell lines 293-FIT-ETTh and 293-FIT-NT (original cell line, not transfected), grown as monolayers in 6 cm diameter polystyrol dishes and induced with 1 µg/ml doxycycline for 20 h, were incubated for 1 min at 37° C. with 2 ml of a mixture of human plasma (50%) and KRH buffer (50%). KRH buffer (Krebs-Ringer-Henseleit) contains 5.6 mM (+)-Glucose, 125 mM NaCl, 4.8 mM KCl, 1.2 mM $KH_2PO_4$, 1.2 mM $CaCl_2$, 1.2 mM $MgSO_4$, and 25 mM HEPES-NaOH pH 7.4. The dishes were rinsed 4 times with 3 ml ice-cold KRH and subsequently incubated with 1 ml of 4 mmol/l $HClO_4$ to release the cell contents. 15 µl of lysate were analyzed by LC-MS (ESI, positive mode) using a Thermo Finnigan TSQ Quantum triple quad mass spectrometer equipped with a Waters Atlantis HILIC silica column (length 100 mm, diameter 3 mm, particle size 5 µm). The solvent for isocratic chromatography (flow rate 250 µl/min) was made of methanol (70%) and 0.1% formic acid (30%). Data sets were compared by LC-MS Difference Shading software (see separate patent application). An ETTh-specific peak was observed at m/z=144 and t=5 min. Because of the positive mode of LC-MS operation, it was clear that the unknown substrate is positively charged, at least in an acid solvent. In addition, a $K^+$ echo at m/z=182 (this results from replacing $H^+$ with $K^+$) suggested a COOH moiety. LC-MS/MS fragmentation of the unknown compound yielded two major fragments at m/z=84 and 58. With an appropriate molecular mass, stachydrine (alias proline betaine; $C_7H_{14}NO_2$ in acid solvent; CAS 471-87-4 (inner salt), CAS 4136-37-2 (hydrochloride)) was a candidate (FIG. 4). Indeed, stachydrine (bought from Extrasynthese, France) gave fragments identical to the unknown substrate. Finally, 293-FIT-ETTh cell monolayers, by contrast to control 293-FIT-NT cells, accumulated stachydrine when incubated with 10 µmol/l stachydrine in KRH for 1 min at 37° C.

Example 3

Determination of the Key Substrate of ETT

Figure 2:
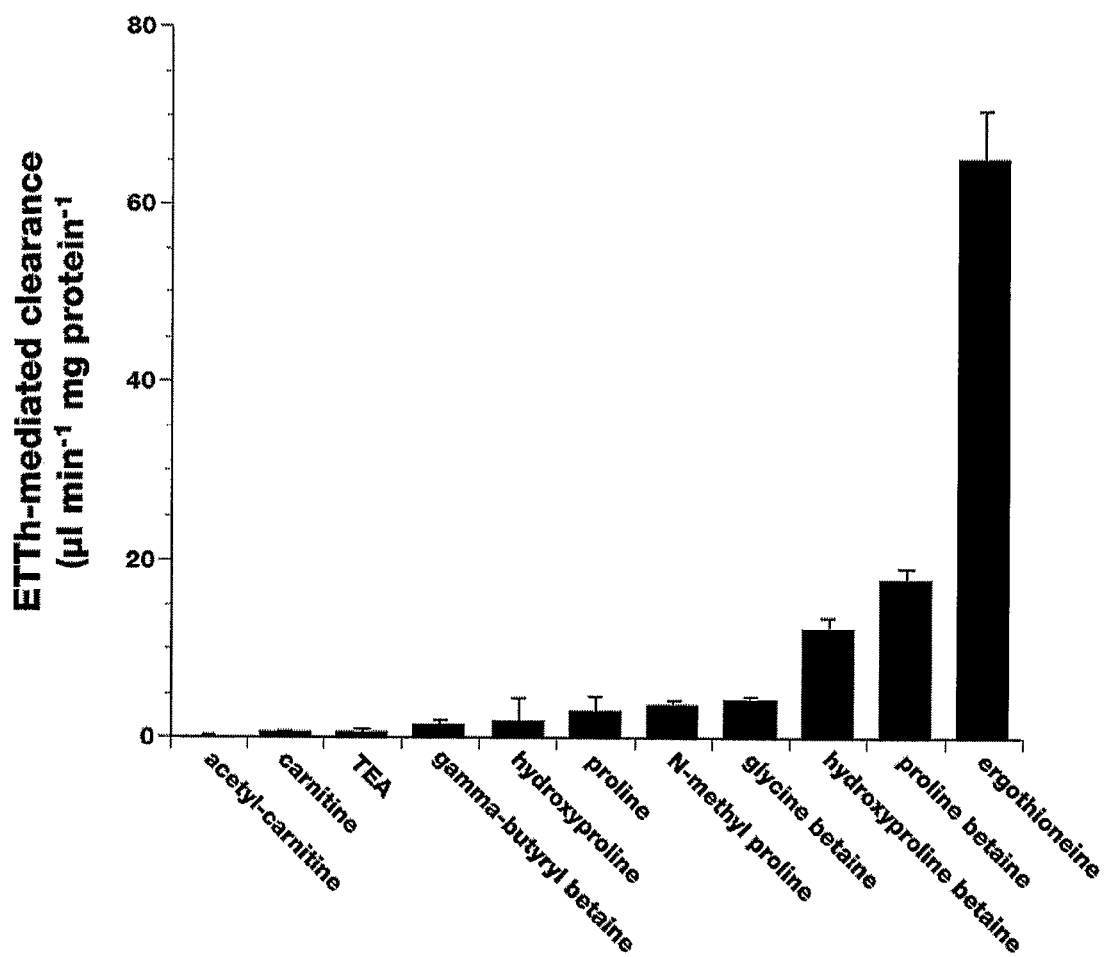
FIG. 2: Transport efficiency profile of ETTh. Substrate concentration was 10 µmol/l for all LC-MS/MS assays (gamma-butyryl betaine, N-methyl proline (alias hygric acid), hydroxyproline betaine (alias betonicine), proline betaine (alias stachydrine), and ergothioneine) and 0.1 µmol/l for all radiotracer assays.

A series of compounds structurally related to either stachydrine or carnitine, the key substrate of the related OCTN2 transporter was tested, for transport by ETTh. FIG. 2 shows results both from radiotracer and LC-MS/MS assays. For some compounds like e.g. glycine betaine and proline, it was not possible to determine ETTh-mediated transport by LC-MS/MS because of the high intracellular levels of these compounds. LC-MS/MS determines total cellular content of a particular analyte. To calculate transport into the cells (=uptake), it is necessary to incubate cells with and without substrate and then to take the difference of cellular content. If the endogenous cellular content is very high, small increments due to transport will not be noticeable. By contrast, with a radiolabeled substrate applied to the incubation medium, radioactivity in the cell lysate directly represents uptake. In both assays, uptake into control cells must be subtracted from uptake into cells expressing the transporter to calculate specific uptake, i.e. transporter-mediated substrate transfer.

Figure 3:
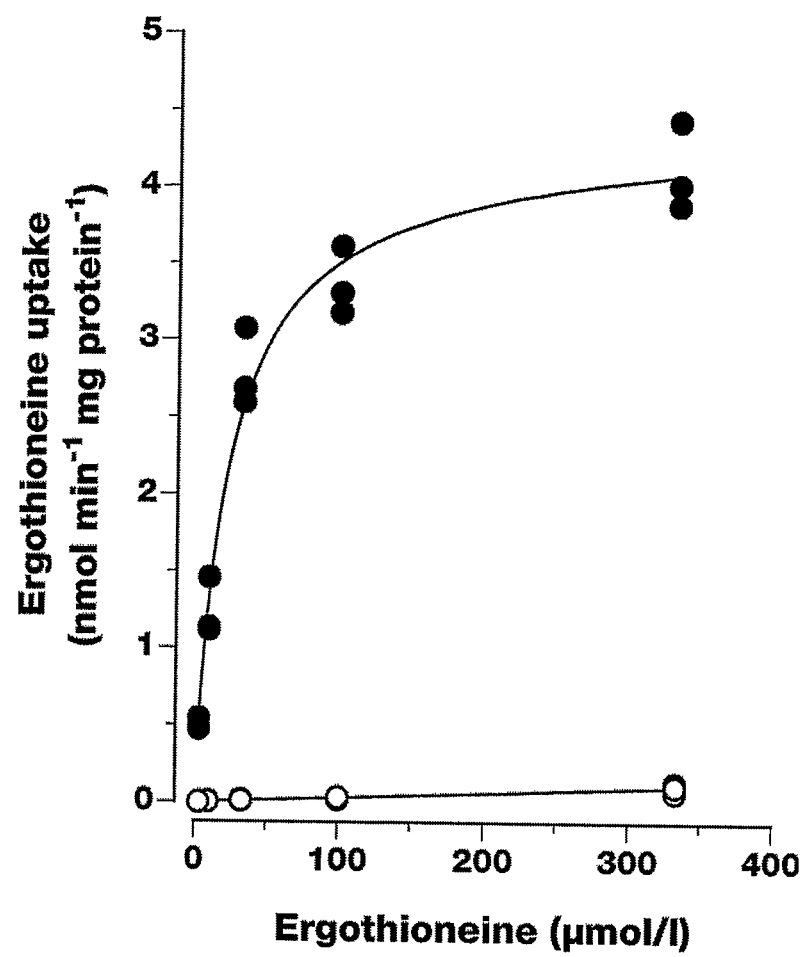
FIG. 3: Determination of $K_m$ and $V_{max}$ of ergothioneine transport via ETTh. 293-FIT-ETTh (filled circles) or 293-FIT-NT (open circles) cell monolayers were incubated for 1 min at 37° C. with various ET concentrations in KRH buffer. After thorough washing, cells were lysed with 4 mmol/l $HClO_4$. Lysates were analysed for ET content by LC-MS/MS. Each circle represents a single dish. Uptake into control cells was modeled with a straight line through the origin. Uptake into ETTh-expressing cells was modeled with $v=V_{max}*S/(K_m+S)+d*S$, where S is the substrate concentration, and d is the slope of the line determined with control cells (=0.32 µl/min/mg protein).

In FIG. 2, the clearance was calculated by dividing the velocity of uptake by the substrate concentration. If the substrate concentration is much smaller than the affinity of the transporter ($=K_m$), then the clearance is directly proportional to the transport efficiency, defined, by analogy to catalytic efficiency for enzymes, as $k_{cat}/K_m$, where $k_{cat}$ is the turnover number of an individual transporter molecule (note that $V_{max}=k_{cat}*E_{total}$, where $E_{total}$ is the number of transporter molecules). The transport efficiency rather than the affinity must be used to judge whether a compound is a good or poor substrate for a given transporter. From the data obtained in the experiments of the present invention it was inferred that for significant transport rates, substrates of ETT must contain the glycine betaine moiety (FIG. 4). A search of the Beilstein library with this moiety revealed ergothioneine (ET; alias thiohistidine betaine; $M_r$=229.3) as a further substrate candidate known to be present regularly in humans and other mammalian species. A test of 293-FIT-ETTh cells with this compound bought from Bachem, Switzerland, revealed extremely high transport activity (FIG. 2). By contrast, the carnitine transporter OCTN2 from rat, did not accept ET as a substrate at all. Moreover, for ETTh a $K_m$ of 22 µmol/l was determined for ET (FIG. 3), which is a very high affinity for a transport protein. Since 10 µmol/l ET, which then is close to half-saturation, was used in the experiment for FIG. 2, the value for ET of FIG. 2 underestimates the true power of ETT for this substrate. Indeed, $V_{max}$ (=4.2 nmol/min/mg protein) divided by $K_m$ yields a true clearance of 190 µl/min/mg protein. For the second best substrate, stachydrine, no such correction is necessary, since the affinity of ETTh for stachydrine is only 300 µmol/l. Thus, ETTh transports ET 10-fold better than stachydrine, and physiological ET transport will hardly be affected by stachydrine, since the latter was detected at plasma levels of about 10 µmol/l in humans. Without expression of ETT, there is virtually no uptake of ET into cells (cf. FIG. 3). In conclusion, it could be established that ergothioneine is the key substrate of ETT. Transport of the hitherto suggested substrate TEA is negligible. Similar results were obtained with ETT from rat.

Example 4

Quantitative Determination of Intracellular ET by LC-MS/MS

Cell monolayers in 6 cm diameter plastic dishes were washed 4 times with 3 ml each of ice-cold KRH buffer and then incubated 30 min with 1 ml 4 mmol/l $HClO_4$ to release cellular contents. 20 µl of lysate were analyzed by LC-MS/MS selected reaction monitoring (SRM; ESI, positive mode) using a Thermo Finnigan TSQ Quantum triple quad mass spectrometer equipped with a Waters Atlantis HILIC silica column (length 100 mm, diameter 3 mm, particle size 5 µm). The solvent for isocratic chromatography (flow rate 250 µl/min) was made of methanol (70%) and 0.1% formic acid (30%). Parent and fragment mass charge ratios were set to 230 and 186 (collision energy 16 V) or 127 (collision energy 24 V), respectively. The peak area for ET (peak retention time 3.8 min) was integrated and divided by the peak area of an internal standard (1-methyl-4-phenyl pyridinium; parent 170, fragment 128, collision energy 25 V) to yield the ET response ratio. Standards were mixed by using control cell lysates prepared as above as solvent. A standard curve was fit to the reference data by weighted linear regression. Sample ET content was calculated with the ET response ratio and the slope of the regression line. Protein content of cell lysates was estimated from the response ratio for proline (parent 116, fragment 70, collision energy 24 V), which was calibrated with 4-6 matched cell monolayer dishes that were analysed for protein content by the bichinonic acid assay.

The invention claimed is:

1. A method for identifying and/or obtaining a compound capable of modulating ergothioneine transport comprising:
   (a) contacting a test compound with a system for measuring ergothioneine transport activity, wherein said system comprises an ergothioneine transporter (ETT) polypeptide or a functional fragment thereof having at least 95% identity to the full length of SEQ ID NO:2, and a substrate for measuring ergothioneine transport by the system, wherein the substrate is selected from the group consisting of ergothioneine, proline betaine, hydroxyproline betaine or a derivative or analog of any one thereof; and
   (b) detecting an altered level of the ergothioneine transport activity of the ETT polypeptide or functional fragment in the presence of the test compound compared to the ergothioneine transport activity in the absence of the test compound and/or presence of a control; and
   (c) correlating an increase or reduction in said level of the ergothioneine transport activity with a compound that functions as an ergothioneine transport modulator.

2. The method of claim 1, wherein the compound enhances the transporter function of ETT.

3. The method of claim 1, wherein the compound reduces or blocks the transporter function of ETT.

* * * * *

```
                        SEQUENCE LISTING

<160> NUMBER OF SEQ ID NOS: 2

<210> SEQ ID NO 1
<211> LENGTH: 2166
<212> TYPE: DNA
<213> ORGANISM: Homo sapiens
<220> FEATURE:
<221> NAME/KEY: CDS
<222> LOCATION: (159)..(1814)

<400> SEQUENCE: 1
cccaggaacg gtccccggct tcgcgcccca atttctaaca gcctgcctgt ccccgggaa        60 cgttctaaca tccttgggga gcgccccagc tacaagacac tgtcctgaga acgctgtcat      120
cacccgtagt tgcaagtttc ggagcggcag tgggaagc atg cgg gac tac gac gag     176
                                          Met Arg Asp Tyr Asp Glu
                                            1               5 gtg atc gcc ttc ctg ggc gag tgg ggg ccc ttc cag cgc ctc atc ttc        224
Val Ile Ala Phe Leu Gly Glu Trp Gly Pro Phe Gln Arg Leu Ile Phe
         10                  15                  20 ttc ctg ctc agc gcc agc atc atc ccc aat ggc ttc aat ggt atg tca        272
Phe Leu Leu Ser Ala Ser Ile Ile Pro Asn Gly Phe Asn Gly Met Ser
     25                  30                  35 gtc gtg ttc ctg gcg ggg acc ccg gag cac cgc tgt cga gtg ccg gac        320
Val Val Phe Leu Ala Gly Thr Pro Glu His Arg Cys Arg Val Pro Asp
 40                  45                  50 gcc gcg aac ctg agc agc gcc tgg cgc aac aac agt gtc ccg ctg cgg        368
Ala Ala Asn Leu Ser Ser Ala Trp Arg Asn Asn Ser Val Pro Leu Arg
55                  60                  65                  70 ctg cgg gac ggc cgc gag gtg ccc cac agc tgc agc cgc tac cgg ctc        416
Leu Arg Asp Gly Arg Glu Val Pro His Ser Cys Ser Arg Tyr Arg Leu
                 75                  80                  85 gcc acc atc gcc aac ttc tcg gcg ctc ggg ctg gag ccg ggg cgc gac        464
Ala Thr Ile Ala Asn Phe Ser Ala Leu Gly Leu Glu Pro Gly Arg Asp
             90                  95                 100 gtg gac ctg ggg cag ctg gag cag gag agc tgc ctg gat ggc tgg gag        512
Val Asp Leu Gly Gln Leu Glu Gln Glu Ser Cys Leu Asp Gly Trp Glu
        105                 110                 115 ttc agc cag gac gtc tac ctg tcc acc gtc gtg acc gag tgg aat ctg        560
Phe Ser Gln Asp Val Tyr Leu Ser Thr Val Val Thr Glu Trp Asn Leu
    120                 125                 130 gtg tgt gag gac aac tgg aag gtg ccc ctc acc acc tcc ctg ttc ttc        608
Val Cys Glu Asp Asn Trp Lys Val Pro Leu Thr Thr Ser Leu Phe Phe
135                 140                 145                 150 gta ggc gtg ctc ctc ggc tcc ttc gtg tcc ggg cag ctg tca gac agg        656
Val Gly Val Leu Leu Gly Ser Phe Val Ser Gly Gln Leu Ser Asp Arg
                155                 160                 165 ttt ggc agg aag aac gtt ctc ttc gca acc atg gct gta cag act ggc        704
Phe Gly Arg Lys Asn Val Leu Phe Ala Thr Met Ala Val Gln Thr Gly
            170                 175                 180 ttc agc ttc ctg cag att ttc tcc atc agc tgg gag atg ttc act gtg        752
Phe Ser Phe Leu Gln Ile Phe Ser Ile Ser Trp Glu Met Phe Thr Val
        185                 190                 195 tta ttt gtc atc gtg ggc atg ggc cag atc tcc aac tat gtg gta gcc        800
Leu Phe Val Ile Val Gly Met Gly Gln Ile Ser Asn Tyr Val Val Ala
```

-continued

|     |     |     |     | 200 |     |     |     |     | 205 |     |     |     |     | 210 |     |     |      |
|-----|-----|-----|-----|-----|-----|-----|-----|-----|-----|-----|-----|-----|-----|-----|-----|-----|------|
| ttc | ata | cta | gga | aca | gaa | att | ctt | ggc | aag | tca | gtt | cgt | att | ata | ttc |     | 848  |
| Phe | Ile | Leu | Gly | Thr | Glu | Ile | Leu | Gly | Lys | Ser | Val | Arg | Ile | Ile | Phe |     |      |
| 215 |     |     |     | 220 |     |     |     |     | 225 |     |     |     |     | 230 |     |     |      |

| tct | aca | tta | gga | gtg | tgc | aca | ttt | ttt | gca | gtt | ggc | tat | atg | ctg | ctg |     | 896 |
|-----|-----|-----|-----|-----|-----|-----|-----|-----|-----|-----|-----|-----|-----|-----|-----|-----|-----|
| Ser | Thr | Leu | Gly | Val | Cys | Thr | Phe | Phe | Ala | Val | Gly | Tyr | Met | Leu | Leu |     |     |
|     |     |     |     | 235 |     |     |     |     | 240 |     |     |     |     | 245 |     |     |     |

| cca | ctg | ttt | gct | tac | ttc | atc | aga | gac | tgg | cgg | atg | ctg | ctg | ctg | gcg |     | 944 |
|-----|-----|-----|-----|-----|-----|-----|-----|-----|-----|-----|-----|-----|-----|-----|-----|-----|-----|
| Pro | Leu | Phe | Ala | Tyr | Phe | Ile | Arg | Asp | Trp | Arg | Met | Leu | Leu | Leu | Ala |     |     |
|     |     |     |     | 250 |     |     |     |     | 255 |     |     |     |     | 260 |     |     |     |

| ctg | acg | gtg | ccg | gga | gtg | ctg | tgt | gtc | ccg | ctg | tgg | tgg | ttc | att | cct |     | 992  |
|-----|-----|-----|-----|-----|-----|-----|-----|-----|-----|-----|-----|-----|-----|-----|-----|-----|------|
| Leu | Thr | Val | Pro | Gly | Val | Leu | Cys | Val | Pro | Leu | Trp | Trp | Phe | Ile | Pro |     |      |
|     |     |     |     | 265 |     |     |     |     | 270 |     |     |     |     | 275 |     |     |      |

| gaa | tct | ccc | cga | tgg | ctg | ata | tcc | cag | aga | aga | ttt | aga | gag | gct | gaa |     | 1040 |
|-----|-----|-----|-----|-----|-----|-----|-----|-----|-----|-----|-----|-----|-----|-----|-----|-----|------|
| Glu | Ser | Pro | Arg | Trp | Leu | Ile | Ser | Gln | Arg | Arg | Phe | Arg | Glu | Ala | Glu |     |      |
|     |     |     |     | 280 |     |     |     |     | 285 |     |     |     |     | 290 |     |     |      |

| gat | atc | atc | caa | aaa | gct | gca | aaa | atg | aac | aac | ata | gct | gta | cca | gca |     | 1088 |
|-----|-----|-----|-----|-----|-----|-----|-----|-----|-----|-----|-----|-----|-----|-----|-----|-----|------|
| Asp | Ile | Ile | Gln | Lys | Ala | Ala | Lys | Met | Asn | Asn | Ile | Ala | Val | Pro | Ala |     |      |
| 295 |     |     |     | 300 |     |     |     |     | 305 |     |     |     |     | 310 |     |     |      |

| gtg | ata | ttt | gat | tct | gtg | gag | gag | cta | aat | ccc | ctg | aag | cag | cag | aaa |     | 1136 |
|-----|-----|-----|-----|-----|-----|-----|-----|-----|-----|-----|-----|-----|-----|-----|-----|-----|------|
| Val | Ile | Phe | Asp | Ser | Val | Glu | Glu | Leu | Asn | Pro | Leu | Lys | Gln | Gln | Lys |     |      |
|     |     |     |     | 315 |     |     |     |     | 320 |     |     |     |     | 325 |     |     |      |

| gct | ttc | att | ctg | gac | ctg | ttc | agg | act | cgg | aat | att | gcc | ata | atg | acc |     | 1184 |
|-----|-----|-----|-----|-----|-----|-----|-----|-----|-----|-----|-----|-----|-----|-----|-----|-----|------|
| Ala | Phe | Ile | Leu | Asp | Leu | Phe | Arg | Thr | Arg | Asn | Ile | Ala | Ile | Met | Thr |     |      |
|     |     |     |     | 330 |     |     |     |     | 335 |     |     |     |     | 340 |     |     |      |

| att | atg | tct | ttg | ctg | cta | tgg | atg | ctg | acc | tca | gtg | ggt | tac | ttt | gct |     | 1232 |
|-----|-----|-----|-----|-----|-----|-----|-----|-----|-----|-----|-----|-----|-----|-----|-----|-----|------|
| Ile | Met | Ser | Leu | Leu | Leu | Trp | Met | Leu | Thr | Ser | Val | Gly | Tyr | Phe | Ala |     |      |
|     |     |     |     | 345 |     |     |     |     | 350 |     |     |     |     | 355 |     |     |      |

| ctg | tct | ctg | gat | gct | cct | aat | tta | cat | gga | gat | gcc | tac | ctg | aac | tgt |     | 1280 |
|-----|-----|-----|-----|-----|-----|-----|-----|-----|-----|-----|-----|-----|-----|-----|-----|-----|------|
| Leu | Ser | Leu | Asp | Ala | Pro | Asn | Leu | His | Gly | Asp | Ala | Tyr | Leu | Asn | Cys |     |      |
| 360 |     |     |     | 365 |     |     |     |     | 370 |     |     |     |     |     |     |     |      |

| ttc | ctc | tct | gcc | ttg | att | gaa | att | cca | gct | tac | att | aca | gcc | tgg | ctg |     | 1328 |
|-----|-----|-----|-----|-----|-----|-----|-----|-----|-----|-----|-----|-----|-----|-----|-----|-----|------|
| Phe | Leu | Ser | Ala | Leu | Ile | Glu | Ile | Pro | Ala | Tyr | Ile | Thr | Ala | Trp | Leu |     |      |
| 375 |     |     |     | 380 |     |     |     |     | 385 |     |     |     |     | 390 |     |     |      |

| cta | ttg | cga | acc | ctg | ccc | agg | cgt | tat | atc | ata | gct | gca | gta | ctg | ttc |     | 1376 |
|-----|-----|-----|-----|-----|-----|-----|-----|-----|-----|-----|-----|-----|-----|-----|-----|-----|------|
| Leu | Leu | Arg | Thr | Leu | Pro | Arg | Arg | Tyr | Ile | Ile | Ala | Ala | Val | Leu | Phe |     |      |
|     |     |     |     | 395 |     |     |     |     | 400 |     |     |     |     | 405 |     |     |      |

| tgg | gga | gga | ggt | gtg | ctt | ctc | ttc | att | caa | ctg | gta | cct | gtg | gat | tat |     | 1424 |
|-----|-----|-----|-----|-----|-----|-----|-----|-----|-----|-----|-----|-----|-----|-----|-----|-----|------|
| Trp | Gly | Gly | Gly | Val | Leu | Leu | Phe | Ile | Gln | Leu | Val | Pro | Val | Asp | Tyr |     |      |
|     |     |     |     | 410 |     |     |     |     | 415 |     |     |     |     | 420 |     |     |      |

| tac | ttc | tta | tcc | att | ggt | ctg | gtc | atg | ctg | gga | aaa | ttt | ggg | atc | acc |     | 1472 |
|-----|-----|-----|-----|-----|-----|-----|-----|-----|-----|-----|-----|-----|-----|-----|-----|-----|------|
| Tyr | Phe | Leu | Ser | Ile | Gly | Leu | Val | Met | Leu | Gly | Lys | Phe | Gly | Ile | Thr |     |      |
|     |     |     |     | 425 |     |     |     |     | 430 |     |     |     |     | 435 |     |     |      |

| tct | gct | ttc | tcc | atg | ctg | tat | gtc | ttc | act | gct | gag | ctc | tac | cca | acc |     | 1520 |
|-----|-----|-----|-----|-----|-----|-----|-----|-----|-----|-----|-----|-----|-----|-----|-----|-----|------|
| Ser | Ala | Phe | Ser | Met | Leu | Tyr | Val | Phe | Thr | Ala | Glu | Leu | Tyr | Pro | Thr |     |      |
|     |     |     |     | 440 |     |     |     |     | 445 |     |     |     |     | 450 |     |     |      |

| ctg | gtc | agg | aac | atg | gcg | gtg | ggg | gtc | aca | tcc | acg | gcc | tcc | aga | gtg |     | 1568 |
|-----|-----|-----|-----|-----|-----|-----|-----|-----|-----|-----|-----|-----|-----|-----|-----|-----|------|
| Leu | Val | Arg | Asn | Met | Ala | Val | Gly | Val | Thr | Ser | Thr | Ala | Ser | Arg | Val |     |      |
| 455 |     |     |     | 460 |     |     |     |     | 465 |     |     |     |     | 470 |     |     |      |

| ggc | agc | atc | att | gcc | ccc | tac | ttt | gtt | tac | ctc | ggt | gct | tac | aac | aga |     | 1616 |
|-----|-----|-----|-----|-----|-----|-----|-----|-----|-----|-----|-----|-----|-----|-----|-----|-----|------|
| Gly | Ser | Ile | Ile | Ala | Pro | Tyr | Phe | Val | Tyr | Leu | Gly | Ala | Tyr | Asn | Arg |     |      |
|     |     |     |     | 475 |     |     |     |     | 480 |     |     |     |     | 485 |     |     |      |

| atg | ctg | ccc | tac | atc | gtc | atg | ggt | agt | ctg | act | gtc | ctg | att | gga | atc |     | 1664 |
|-----|-----|-----|-----|-----|-----|-----|-----|-----|-----|-----|-----|-----|-----|-----|-----|-----|------|
| Met | Leu | Pro | Tyr | Ile | Val | Met | Gly | Ser | Leu | Thr | Val | Leu | Ile | Gly | Ile |     |      |
|     |     |     |     | 490 |     |     |     |     | 495 |     |     |     |     | 500 |     |     |      |

| ctc | acc | ctt | ttt | ttc | cct | gaa | agt | ttg | gga | atg | act | ctt | cca | gaa | acc |     | 1712 |
|-----|-----|-----|-----|-----|-----|-----|-----|-----|-----|-----|-----|-----|-----|-----|-----|-----|------|
| Leu | Thr | Leu | Phe | Phe | Pro | Glu | Ser | Leu | Gly | Met | Thr | Leu | Pro | Glu | Thr |     |      |
|     |     |     |     | 505 |     |     |     |     | 510 |     |     |     |     | 515 |     |     |      |

| tta | gag | cag | atg | cag | aaa | gtg | aaa | tgg | ttc | aga | tct | ggg | aaa | aaa | aca |     | 1760 |
|-----|-----|-----|-----|-----|-----|-----|-----|-----|-----|-----|-----|-----|-----|-----|-----|-----|------|
| Leu | Glu | Gln | Met | Gln | Lys | Val | Lys | Trp | Phe | Arg | Ser | Gly | Lys | Lys | Thr |     |      |

```
                 520                 525                 530
aga gac tca atg gag aca gaa gaa aat ccc aag gtt cta ata act gca    1808
Arg Asp Ser Met Glu Thr Glu Glu Asn Pro Lys Val Leu Ile Thr Ala
535                 540                 545                 550 ttc tga aaaatatct accccatttg gtgaagtgaa aacagaaaaa ataagaccct      1864
Phe gtggagaaat tcgttgttcc cactgaaatg gactgactgt aacgattgac accaaaatga  1924
accttgctat caagaaatgc tcgtcataca gtaaactctg gatgattctt ccagataatg  1984
tccttgcttt acaaccaac catttctaga gagtctcctt actcattaat tcaatgaaat   2044
ggattggtaa gatgtcttga aacatgtta gtcaaggact ggtaaaatac atataaagat   2104
taacactcat ttccaatcat acaaatacta tccaaataaa aataacatca ttgtattaac  2164
gc                                                                  2166

<210> SEQ ID NO 2
<211> LENGTH: 551
<212> TYPE: PRT
<213> ORGANISM: Homo sapiens

<400> SEQUENCE: 2

Met Arg Asp Tyr Asp Glu Val Ile Ala Phe Leu Gly Glu Trp Gly Pro
1               5                   10                  15

Phe Gln Arg Leu Ile Phe Phe Leu Leu Ser Ala Ser Ile Ile Pro Asn
                20                  25                  30

Gly Phe Asn Gly Met Ser Val Val Phe Leu Ala Gly Thr Pro Glu His
            35                  40                  45

Arg Cys Arg Val Pro Asp Ala Ala Asn Leu Ser Ser Ala Trp Arg Asn
        50                  55                  60

Asn Ser Val Pro Leu Arg Leu Arg Asp Gly Arg Glu Val Pro His Ser
65                  70                  75                  80

Cys Ser Arg Tyr Arg Leu Ala Thr Ile Ala Asn Phe Ser Ala Leu Gly
                85                  90                  95

Leu Glu Pro Gly Arg Asp Val Asp Leu Gly Gln Leu Glu Gln Glu Ser
                100                 105                 110

Cys Leu Asp Gly Trp Glu Phe Ser Gln Asp Val Tyr Leu Ser Thr Val
            115                 120                 125

Val Thr Glu Trp Asn Leu Val Cys Glu Asp Asn Trp Lys Val Pro Leu
130                 135                 140

Thr Thr Ser Leu Phe Phe Val Gly Val Leu Leu Gly Ser Phe Val Ser
145                 150                 155                 160

Gly Gln Leu Ser Asp Arg Phe Gly Arg Lys Asn Val Leu Phe Ala Thr
                165                 170                 175

Met Ala Val Gln Thr Gly Phe Ser Phe Leu Gln Ile Phe Ser Ile Ser
            180                 185                 190

Trp Glu Met Phe Thr Val Leu Phe Val Ile Val Gly Met Gly Gln Ile
        195                 200                 205

Ser Asn Tyr Val Val Ala Phe Ile Leu Gly Thr Glu Ile Leu Gly Lys
    210                 215                 220

Ser Val Arg Ile Ile Phe Ser Thr Leu Gly Val Cys Thr Phe Phe Ala
225                 230                 235                 240

Val Gly Tyr Met Leu Leu Pro Leu Phe Ala Tyr Phe Ile Arg Asp Trp
                245                 250                 255

Arg Met Leu Leu Leu Ala Leu Thr Val Pro Gly Val Leu Cys Val Pro
            260                 265                 270
```

-continued

```
Leu Trp Trp Phe Ile Pro Glu Ser Pro Arg Trp Leu Ile Ser Gln Arg
        275                 280                 285

Arg Phe Arg Glu Ala Glu Asp Ile Ile Gln Lys Ala Ala Lys Met Asn
        290                 295                 300

Asn Ile Ala Val Pro Ala Val Ile Phe Asp Ser Val Glu Glu Leu Asn
305                 310                 315                 320

Pro Leu Lys Gln Gln Lys Ala Phe Ile Leu Asp Leu Phe Arg Thr Arg
                    325                 330                 335

Asn Ile Ala Ile Met Thr Ile Met Ser Leu Leu Leu Trp Met Leu Thr
                340                 345                 350

Ser Val Gly Tyr Phe Ala Leu Ser Leu Asp Ala Pro Asn Leu His Gly
            355                 360                 365

Asp Ala Tyr Leu Asn Cys Phe Leu Ser Ala Leu Ile Glu Ile Pro Ala
        370                 375                 380

Tyr Ile Thr Ala Trp Leu Leu Arg Thr Leu Pro Arg Arg Tyr Ile
385                 390                 395                 400

Ile Ala Ala Val Leu Phe Trp Gly Gly Val Leu Leu Phe Ile Gln
                    405                 410                 415

Leu Val Pro Val Asp Tyr Tyr Phe Leu Ser Ile Gly Leu Val Met Leu
                420                 425                 430

Gly Lys Phe Gly Ile Thr Ser Ala Phe Ser Met Leu Tyr Val Phe Thr
            435                 440                 445

Ala Glu Leu Tyr Pro Thr Leu Val Arg Asn Met Ala Val Gly Val Thr
    450                 455                 460

Ser Thr Ala Ser Arg Val Gly Ser Ile Ile Ala Pro Tyr Phe Val Tyr
465                 470                 475                 480

Leu Gly Ala Tyr Asn Arg Met Leu Pro Tyr Ile Val Met Gly Ser Leu
                485                 490                 495

Thr Val Leu Ile Gly Ile Leu Thr Leu Phe Phe Pro Glu Ser Leu Gly
                500                 505                 510

Met Thr Leu Pro Glu Thr Leu Glu Gln Met Gln Lys Val Lys Trp Phe
        515                 520                 525

Arg Ser Gly Lys Lys Thr Arg Asp Ser Met Glu Thr Glu Glu Asn Pro
    530                 535                 540

Lys Val Leu Ile Thr Ala Phe
545                 550
```